(12) United States Patent
Schneider et al.

(10) Patent No.: US 7,349,834 B2
(45) Date of Patent: Mar. 25, 2008

(54) MOLECULAR MOTOR

(75) Inventors: Thomas D. Schneider, Frederick, MD (US); Ilya Gennadiyevich Lyakhov, Frederick, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 148 days.

(21) Appl. No.: 10/061,377

(22) Filed: Feb. 1, 2002

(65) Prior Publication Data

US 2002/0083710 A1  Jul. 4, 2002

Related U.S. Application Data

(63) Continuation-in-part of application No. PCT/US00/20925, filed on Jul. 31, 2000.

(60) Provisional application No. 60/146,975, filed on Aug. 3, 1999.

(51) Int. Cl.
   *G06G 7/48* (2006.01)
(52) U.S. Cl. .................. 703/11; 530/350; 435/283.1
(58) Field of Classification Search ................ 422/129; 702/19, 27; 703/11
   See application file for complete search history.

(56) References Cited

U.S. PATENT DOCUMENTS 5,499,547 A * 3/1996 Nagai et al. ............... 74/89.34
5,761,960 A   6/1998 Nagai et al.

FOREIGN PATENT DOCUMENTS

WO   WO 96/30508   10/1996

OTHER PUBLICATIONS

Oplatka. "Are Rotors at the Heart of All Biological Motors?", 1998, Biochemical and Biophysical Research Communications, vol. 246, pp. 301-306.*
"array" definition, Merriam-Webster online dictionary, 2005, on the world wide web at http://www.m-w.com/cgi-bin/dictionary?book=Dictionary&va=array, 2 pages.*
Ganong, Review of Medical Physiology, 1981, Lange Medical Publications, 10th edition, pp. 43-47.*

(Continued)

*Primary Examiner*—Carolyn L. Smith
(74) *Attorney, Agent, or Firm*—Klarquist Sparkman, LLP

(57) ABSTRACT

A molecular motor in which multiple concentric cylinders (or nested cones) rotate around a common longitudinal axis. Opposing complementary surfaces of the cylinders or cones are coated with complementary motor protein pairs (such as actin and myosin). The actin and myosin interact with one another in the presence of ATP to rotate the cylinders or cones relative to one another, and this rotational energy is harnessed to produce work. The concentration of ATP and the number of nested cylinders or cones can be used to control the rotational speed of the motor. The length of the cylinders can also be used to control the power generated by the motor. In another embodiment, the molecular motor includes at least two annular substrates wherein one annular substrate is coated with a first motor protein and the other annular substrate is coated with a second motor protein. The first and second motor proteins interact with each other to move the second annular relative to the first annular substrate.

60 Claims, 9 Drawing Sheets

OTHER PUBLICATIONS

Montemagno et al., "Constructing Biological Motor Powered Nanomechanical Devices," *Nanotechnology*, vol. 10, pp. 225-231 (1999).

Spudich, "How molecular motors work," *Nature*, vol. 372, pp. 515-518 (1994).

Thomas et al., "The physics of biological molecular motors," *J. Phys. D: Appl. Phys.*, vol. 31, pp. 253-266 (1998).

Berg, "The Rotary Motor of Bacterial Flagella," Annu. Rev. Biochem., 72:19-54 (2003).

Blair, "Flagellar Movement Driven by Proton Translocation," FEBS Letters, 545:86-95 (2003).

Ishijima et al., "Simultaneous Observation of Individual ATPase and Mechanical Events by a Single Myosin Molecule During Interaction with Actin," CELL, 92:161-171 (Jan. 23, 1998).

Jaques et al., "Mutations Conferring Resistance to Phenamil and Amiloride, Inhibitors of Sodium-Driven Motility of *Vibrio parahaemolyticus*," Proc. Natl. Acad. Sci. USA, 96:5740-5745 (May 1999).

Kagawa, "Biophysical Studies on ATP Synthase," Adv. Biophys., 36:1-25 (1999).

Kojima et al., "The Bacterial Flagellar Motor: Structure and Functin of a Complex Molecular Machine," International Review of Cytology, 233:93-135 (2004).

Korn et al., "Actin Polymerization and ATP Hydrolysis," SCIENCE, 238:638-644 (1987).

Nicolau et al., "Building Artificial Networks of Protein Molecular Motors," SPIE, 3241:36-46 (1997).

Suzuki et al., "Control of Actin Moving Trajectory by Patterned Poly(methylmethacrylate) Tracks," Biophysical Journal, 72:1997-2001 (May 1997).

Ueno et al., "ATP-Driven Stepwise Rotation of $F_0F_1$-ATP Synthase," Proc. Natl. Acad. Sci. USA, 102(5):1333-1338 (Feb. 1, 2005).

Doering et al., "Rotary DNA Motors," *Biophysical Journal* 69:2258-2267, 1995.

Noji et al., "Direct observation of the rotation of $F_1$-ATPase," *Nature* 386:299-302, 1997.

\* cited by examiner

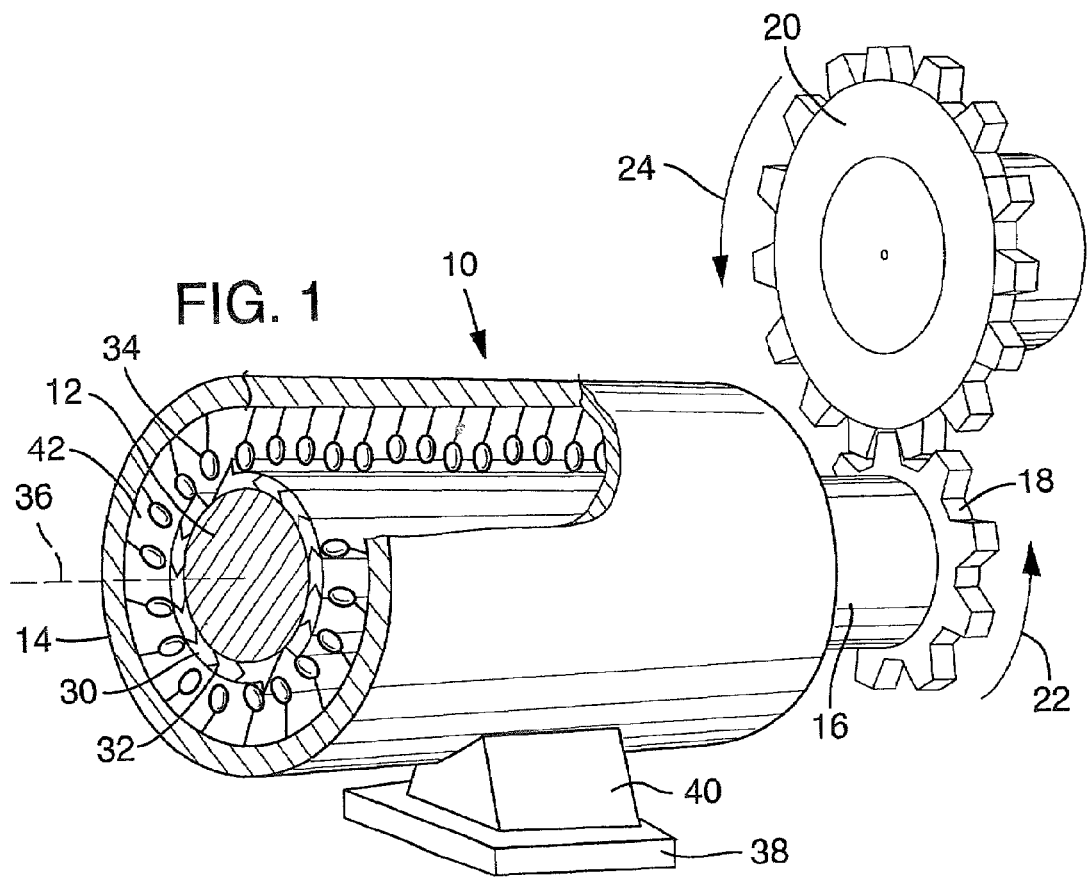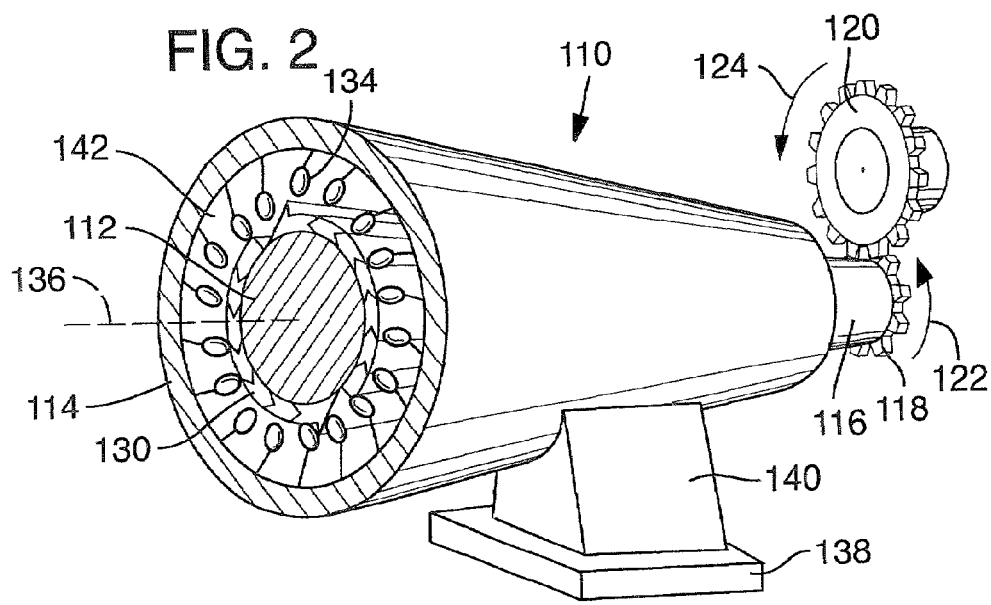

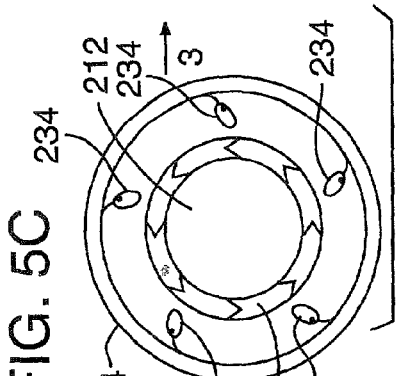
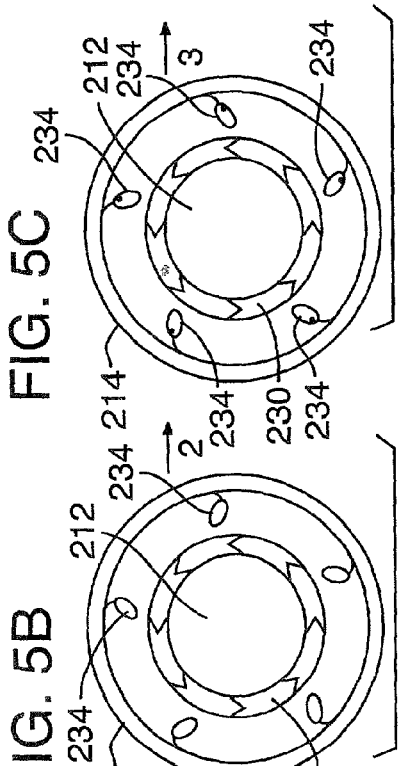
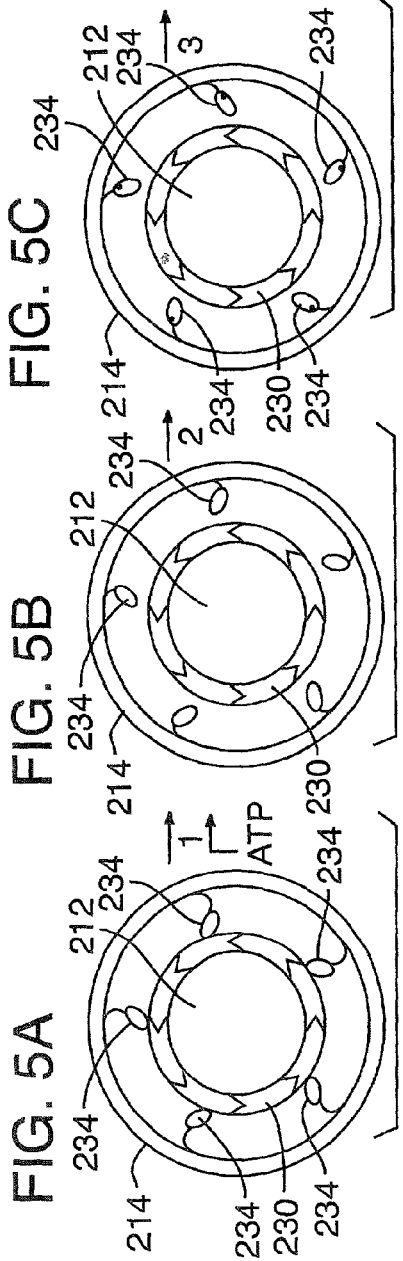

MOLECULAR MOTOR

PRIORITY CLAIM

This application is a continuation-in-part, and claims benefit of PCT Application PCT/US00/20925 filed Jul. 31, 2000, which was published in English under PCT Article 21(2), and designating the U.S., which claims the benefit of U.S. Provisional Application No. 60/146,975 filed Aug. 3, 1999.

FIELD OF THE DISCLOSURE

This disclosure relates to molecular motors, and particularly such motors that are powered by proteins.

BACKGROUND OF THE DISCLOSURE

One of the fundamental properties of biological organisms is the ability to move, or to at least transport cellular components, even on a molecular scale. The biological structure that permits macroscopic movement in animals is muscle, which can be either striated (skeletal), smooth, or cardiac. The molecular structure and function of muscle has been the subject of scientific fascination and research for over a century. As early as the 1840s, William Bowman had suggested that striations in skeletal muscle represented bands of intracellular material with differing refractive indices. These intracellular materials were eventually identified as actin and myosin.

The contractile unit in skeletal muscle is known as a myofibril, which consists of a series of Z-disks to which are attached thin filaments of actin. The Z-disks divide each myofibril into repeating units called sarcomeres, and within each sarcomere is a thick filament of myosin which has heads that can form crossbridges to the actin. In the presence of ATP, the myosin heads undergo a conformational change that causes the cross bridges to link to the actin, and the myosin heads move the actin filaments relative to the myosin filaments. This movement brings the Z-disks closer together, which on a macroscopic level contracts (shortens) the muscle, and implements musculoskeletal function. Although cardiac and smooth muscle differ in their cellular architecture from skeletal muscle, they too rely on the interaction of myosin and actin to contract.

The myosin molecule consists of six polypeptide subunits: two identical heavy chains with a molecular weight of about 200,000 kDa each, and four light chains of about 20 kDa each. In electron micrographs, purified myosin looks like a long thin rod containing two globular heads protruding at one end. This two-headed type of myosin is called myosin II to distinguish it from the smaller, single headed myosin I molecule (having a shorter tail) that is involved in cytoplasmic movements in some nonmuscle cells. The functions of portions of the myosin molecule have been investigated by using the protease trypsin to cleave the myosin II molecule into two fragments called light meromyosin (a coiled tail portion) and heavy meromysin (which contains the globular heads of the molecule, and a portion of the coiled tail). The function of actin and myosin, and their molecular structure, are more fully described in Kendrew, *The Encyclopedia of Molecular Biology*, 1994, pages 688-691; and Kleinsmith and Kish, *Principles of Cell and Molecular Biology*, second edition, 1995, chapter 13, which are incorporated by reference.

A variety of motor proteins other than actin and myosin are also known. The motor protein kinesin, for example, was discovered in 1985 in squid axoplasm. Vale et al., *Cell* 42:39-50, 1985. Kinesin is just one member of a very large family of motor proteins. Endow, *Trends Biochem. Sci.* 16:221-225, 1991; Goldstein, *Trends Cell Biol.* 1:93, 1991; Stewart et al., *Proc. Natl. Acad. Sci. USA* 88:8470-8474, 1991. Another such motor protein is dynein. Li et al., *J. Cell Biol.* 126:1475-1493, 1994. Kinesin, dynein, and related proteins move along microtubules, whereas myosin moves along actin filaments. Like myosin, kinesin is activated by ATP.

Kinesin is composed of two heavy chains (each about 120 kDa) and two light chains (each about 60 kDa). The kinesin heavy chains include three structural domains: (a) an amino-terminal head domain, which contains the sites for ATP and microtubule binding and for motor activity; (b) a middle or stalk domain, which may form an α-helical coiled coil that entwines two heavy chains to form a dimer; and (c) a carboxyl-terminal domain, which probably forms a globular tail that interacts with the light chains and possibly with vesicles and organelles. Kinesin and kinesin-like proteins are all related by sequence similarity within an approximately 340-amino acid region of the head domain, but outside of this conserved region they show no sequence similarity.

Purified motor proteins are capable of generating movement even outside biological organisms. The motility activity of purified kinesin on microtubules has, for example, been demonstrated in vitro. Vale al., *Cell* 42:39-50, 1985. Full-length kinesin heavy chain and several types of truncated kinesin heavy chain molecules produced in *E. coli* are also capable of generating in vitro microtubule motility. Yang et al., *Science* 249:42-47, 1990; Stewart et al., *Proc. Natl. Acad. Sci. USA* 90:5209-5213, 1993. The kinesin motor domain has also been shown to retain motor activity in vitro after genetic fusion to several other proteins including spectrin (Yang et al.), glutathione S-transferase (Stewart et al.), and biotin carboxyl carrier protein (Berliner, 269 *J. Biol. Chem.* 269:8610-8615, 1994).

Similarly, methods have been developed for purification or recombinant production and manipulation of motor proteins, and methods of attaching actin to non-biological substrates are also known. Ishima et al., *Cell* 92:161-171, 1998. Microtubules can be routinely reassembled in vitro from tubulin purified from bovine brains. The nucleation, assembly, and disassembly reactions of microtubules have been well characterized. Cassimeris et al., *Bioessays* 7:149-154, 1987. More recently, recombinant tubulin has been produced in yeast. Davis et al., *Biochemistry* 32:8823-8835, 1993.

Efforts have been made in the past to harness the molecular activity of motor proteins for useful work outside of biological organisms. U.S. Pat. No. 5,830,659, for example, disclosed a system for purifying a molecule of interest from a mixture by aligning microtubules in a separation channel leading out of a liquid reservoir. A kinesin-ligand complex was then added to the liquid reservoir, in the presence of ATP, and the ligand was selected to bind to the molecule of interest in the liquid. When the kinesin came into contact with the microtubules in the channel, the kinesin-ligand (and its bound molecule of interest) were transported through the channel into a collection reservoir, so that the molecule of interest was purified away from the mixture.

Another motor protein device is shown in Japanese patent 5-44298 (JP 5-44298), which describes a pump for moving liquid. Actin is mounted onto a surface of a container in the direction of the desired flow, and meromyosin and ATP are supplied in the liquid. The interaction of the meromyosin and actin "push" the liquid in the direction of flow.

Nicolau et al., *SPIE* 3241:36-46, 1997 discusses constructing a molecular motor or engine using actin and myosin. A rotatable gear is mounted on a stationary base, and the gear has teeth to which arms of actin are attached. Using lithographic techniques of the type used in semiconductor fabrication, a track of myosin is laid down along the peripheral edge of the stationary base so that the arms of actin on the rotatable gear can adhere to the track, and pull the teeth of the gear along the myosin track when ATP is supplied to the system. This arrangement is apparently designed to rotate the gear, and impart rotation to a driven gear that engages the driving gear. However, the myosin track in such a device would be crushed by the teeth of the gear as the gear rotates, or would jam.

Moreover, precise microlithographic positioning of the actin and myosin molecules would be difficult, and perhaps unfeasible, and alignment of the actin arms along the myosin track could not be maintained. It also does not appear that the molecular motor could be scaled up to macroscopic proportions, nor is it clear how the power or speed of the device could be controlled.

It is a goal of certain embodiments of the present disclosure to solve some of the problems of prior approaches by devising a molecular motor that is more easily fabricated, and may if desired be scaled up to macroscopic proportions.

It is also a goal of some embodiments to devise such a molecular motor in which power and speed of the motor can be more conveniently controlled.

SUMMARY OF THE DISCLOSURE

The molecular motor of the present disclosure includes first and second complementary two dimensional arrays of a motor protein, for example adhered to a substrate surface. The first and second arrays of motor proteins are in sufficiently close contact to interact and directionally move one array (and its attached substrate) relative to the other. This action in turn moves a driven member, such as a shaft or gear, to convert the movement into useful power that can produce work.

In some embodiments, there are multiple layers of nested (for example concentric) complementary first and second arrays that interact with one another to directionally move the first and second arrays relative to one another. The arrays may be adhered to a curved surface, such as, for example, a continuous curved surface of rotation having a longitudinal axis and an internal radius (for example a cylinder or cone). Alternatively, the arrays may be adhered to a planar surface of an annular substrate, such as, for example, a disc or a ring. According to a further variation, the arrays may be adhered to a flexible continuous loop surface that can transform between a curved surface and a planar surface as the loop rotates around internal radii. Multiple concentric cylinders, nested cones, concentric rings, or nested loops (which rotate around a common central longitudinal axis) can form a series of complementary surfaces to which the arrays are adhered.

In particular embodiments, the motor proteins are actin and myosin, and the motor includes a source of ATP for activating the myosin to operate the motor. The ATP can be supplied in a liquid that flows longitudinally through the rotatable surfaces on which the arrays are adhered, or the ATP containing liquid may be infused through perforations in surfaces on which the arrays are disposed, to allow permeation of an ATP containing liquid through the surfaces to the motor proteins.

When actin/myosin are the motor proteins, the actin may be applied directionally to a substrate surface and the myosin is applied to a complementary or opposing substrate surface. The actin-coated surface and the myosin-coated surface are in sufficiently close contact that the motor proteins interact to move the surfaces relative to one another, in a direction determined by the directional application of the actin to its surface.

An array of the first motor protein may be coated on a first curved or planar surface, and an array of the second motor protein may be coated on a second complementary curved or planar surface, such that the first and second motor proteins interact to move the second surface in a predetermined direction relative to the first surface. In an illustrative example, one of the arrays is coated on an outer surface of a cylinder, shaft or cone, and another of the arrays is coated on an inner surface of a surrounding structure having a complementary shape that substantially conforms to a shape of the outer surface of the cylinder, shaft or cone. The directional movement of the second surface moves a driver, such as an internal shaft or cylinder in the motor. Alternatively, the driver may be an outer curved surface of the motor (such as an outer surface of an outermost cylinder of the motor). The driven member can take a variety of forms, such as a rotating shaft, a propeller, a wheel, a lever-arm, a gear system, or a pulley system.

An advantage of the disclosed motor is that the arrays can be of a preselected dimension that provides a preselected power output of the motor. For example, the length of a cylinder on which the complementary arrays are coated can be selected to vary the power output. Alternatively, a speed of rotation of the motor can be varied by preselecting the number of multiple nested complementary arrays or the number of stacked, array-coated annular substrates. Alternatively, the speed of rotation can be controlled by altering the concentration of ATP to which the motor proteins are exposed. As the concentration of ATP increases, the speed of the motor will increase up to a maximum speed, at which all the motor proteins are maximally functioning.

In a more specific embodiment, the molecular motor includes a series of concentric tubes or hollow cones, wherein each of the tubes or hollow cones has an outer surface and an inner surface. A first motor protein array (such as an actin array) is attached in a continuous ring of a selected width around the outer surface of each of the tubes or cones, and a second motor protein (such as myosin) is attached in a continuous complementary array of a corresponding width around the inner surface of each of the tubes or cones.

In a further embodiment, the molecular motor includes a first annular substrate defining at least one planar surface coated with a first motor protein and a second annular substrate defining at least one planar surface coated with a second motor protein that interacts with the first motor protein to move the second annular substrate relative to the first annular substrate. The annular substrate may be a thin disc or a ring. For example, the motor may include at least two layers of a plurality of concentric rings. One variant of the annular substrate embodiment includes a stationary substrate, a terminal annular substrate, and at least one intermediate annular substrate interposed between the stationary substrate and the terminal annular substrate. The stationary substrate, terminal annular substrate, and intermediate annular substrate are arranged such that each planar surface coated with a first motor protein is adjacent to a planar surface coated with a second motor protein. A second variant of the annular substrate embodiment includes a stationary member affixed to the first annular substrate and a rotatable member affixed to the second annular substrate wherein the first motor protein can interact with the second motor protein to move the second annular substrate relative to the first annular substrate and consequently rotate the rotatable member.

An additional molecular motor embodiment includes at least one continuous loop of a flexible substrate that defines at least two turning radii and at least one surface that is coated with a first motor protein. Rotation loci members are disposed at the turning radii and at least one of the rotation loci members defines a surface coated with a second motor protein. The interaction of the first motor protein and the second motor protein moves the flexible substrate relative to at least one of the rotation loci members.

The motor proteins can be attached to the surfaces in a variety of ways. The actin, for example, can be expressed by recombinant techniques as a fusion protein with a histidine tag, which is then attached to a nickel-coated surface. Alternatively, the actin can be expressed with an S-tag which binds to an S-protein coated surface, or with a streptavidin tag which binds to biotin on a substrate surface. In another specific, non-limiting example, gelsolin is used to attach the actin to a surface (e.g. see Suzuki et al., *Biophys. J.* 70:401-408, 1996).

In particular embodiments, the first motor protein (for example actin) is directionally attached on the outer surface of a rotatable cylinder or cone in an array that extends both longitudinally along and circumferentially around the tube or cone, and the second motor protein (such as myosin) extends both longitudinally along and circumferentially around the tube or cone in a complementary array of similar size.

The disclosure also describes a method of making a molecular motor, by providing a first continuous curved surface which rotates around a longitudinal axis, and a second curved surface which rotates around the longitudinal axis, and is complementary in shape to the first surface. Another method of making a molecular motor contemplates providing a first annular substrate defining a planar surface and a second annular substrate defining a planar surface, adhering a first motor protein to the planar surface of the first annular substrate and a second motor protein to the planar surface of the second annular substrate, and positioning the first annular substrate relative to the second annular substrate so that the first motor protein can interact with the second motor protein to move the first annular substrate relative to the second annular substrate.

In the disclosed methods, a first motor protein (such as actin) is directionally adhered to the first surface, and a second motor protein (such as myosin) is adhered to the second surface, such that the first and second motor proteins interact to move the first and second surfaces relative to one another. In particular embodiments, the actin is adhered to the surface with a tag (for example a recombinantly expressed tag such as histidine, an S-tag or streptavidin) that interacts with a component of the first surface. The actin may be directionally applied to the planar or first curved surfaces by rotating the planar or curved surface in an actin containing solution.

In certain embodiments, the motor proteins can be portions of actin and myosin that are able to function to move the surfaces relative to one another. For example, heavy meromyosin or myosin I can be used instead of myosin II.

In other embodiments, the motor proteins are microtubules and kinesin, or functional fragments thereof that are sufficient to move the surfaces. The kinesin can be, for example, the N-terminal 410 amino acid residues of kinesin.

The motor of the present disclosure may be a micromachined device constructed on a micrometer-scale, but the motor can also be constructed on a much larger scale by coating larger surfaces with the motor proteins, which can be purified from biological tissues (such as muscle) or produced in large quantities using recombinant techniques.

The molecular motors of the present disclosure are believed to operate much more efficiently than conventional engines that use large temperature differentials or magnetic fields to create rotary motion with energetic efficiencies less than about 35%. The Carnot efficiency of an internal combustion engine is 56%, but other losses reduce the efficiency to about 25%. Many such engines also depend on fossil fuels that create air pollution and may induce global warming as a consequence of the combustion of such fuels.

Muscles use contractile or motor molecules to create macroscopic motion with efficiencies near 70%, and the molecular motors of the present disclosure can use similarly efficient systems to create useful energy. This can be accomplished while producing substantially no pollution, because sugar (or ATP itself) could be used to fuel the motors, and the waste products (ADP and Pi) are biologically useful or biodegradable. In addition, the isothermal conditions under which the motor operates imply low materials stress, and easier construction and maintenance.

The biologically compatible nature of these devices also makes them suitable for medical applications. Biologically based engines can use sugar in the blood (via substrate level phosphorylation glycolysis) as fuel, to replace neuromuscular function lost to diseases such as myasthenia gravis or muscular dystrophy. Alternatively, the motor can be used to perform the mechanical functions of a prosthetic implant.

The foregoing and other objects, features, and advantages of the disclosed molecular motor will become more apparent from the following detailed description of several embodiments which proceeds with reference to the accompanying figures.

BRIEF DESCRIPTION OF THE FIGURES

FIG. 1 is a schematic illustration of one embodiment of the molecular motor, in which actin is directionally applied on an outer surface of a solid internal cylinder, myosin is coated on an internal surface of a surrounding complementary hollow cylinder, and rotation of the internal cylinder drives a rotary gear. Portions of the outer cylinder are broken away to illustrate that the arrays of actin and myosin extend along the length of the device.

FIG. 2 is a schematic illustration similar to FIG. 1, but wherein the surfaces are on cones instead of cylinders.

FIGS. 4A through 4E are successive schematic views illustrating a conventional view of the interaction of actin and a single myosin head, to demonstrate how an actin coated surface is moved by the myosin.

FIGS. 5A through 5E are schematic end views of cylinders similar to those shown in FIG. 1, showing a subset of myosin heads that change conformation substantially in concert to move the internal actin coated cylinder of the motor. Other myosin heads (not shown) are randomly moving through different stages of the conformational changes, without necessarily moving in concert, but only a single subset of myosin heads have been shown for purposes of explanation.

FIG. 12A shows actin directionally applied on one surface of the disc. FIG. 12B shows myosin applied on one surface of the disc.

FIG. 13 includes a plan view of the rings and a side view of multiple ring layers wherein the spatial correspondence between the two views is illustrated by dashed lines.

DETAILED DESCRIPTION OF SEVERAL EMBODIMENTS

Definitions

Figure 3A:
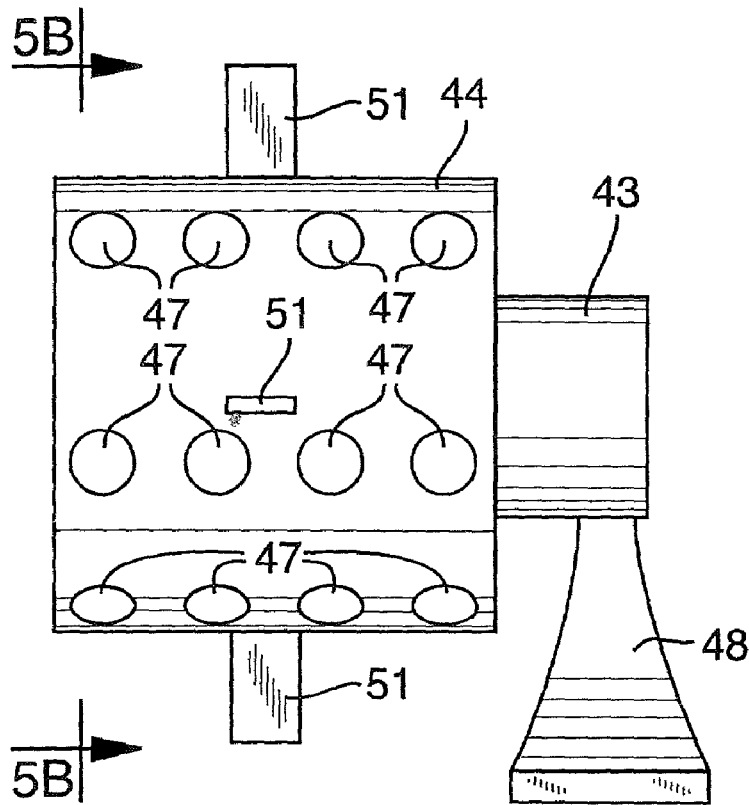
FIG. 3A is a side elevational and FIG. 3B is a cross sectional schematic end view of an alternative embodiment of the disclosure in which the layer of actin surrounds the myosin layer, the inner cylinder is fixed to a stationary bracket, and rotation of the outer cylinder rotates a propeller.

The following definitions and methods are provided to better describe the present disclosure and to guide those of ordinary skill in the art in the practice of the present disclosure. Definitions of common terms may also be found in Rieger et al., *Glossary of Genetics: Classical and Molecular*, 5th edition, Springer-Verlag: New York, 1991; and Lewin, *Genes V*, Oxford University Press: New York, 1994. The standard one and three letter nomenclature for amino acid residues is used (such as H or His for Histidine).

Additional definitions of terms commonly used in molecular genetics can be found in Benjamin Lewin, *Genes V* published by Oxford University Press, 1994 (ISBN 0-19-854287-9); Kendrew et al (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

As used in this specification and the appended claims, the singular forms "a," "an," and "the" include plural referents unless the context clearly dictates otherwise. Thus, for example, reference to a motor comprising "a cylinder" includes a system containing one or more cylinders, and reference to "a motor protein" includes reference to one or more motor proteins.

Micromachining, micromachined, and similar terms refer to the processes used to create micrometer-sized structures with primarily mechanical functions on substrates such as glass, silicon, silica, or a photoreactive polymer-coated chip.

Motor protein means a protein that transduces chemical energy into mechanical force and motion. Such motor proteins often exist in complementary pairs, such as actin and myosin, or kinesin and microtubules. Particular disclosed motor proteins are actin/myosin and kinesin/microtubules. The motor proteins can be used in any form that is capable of transducing the chemical energy (such as the energy of ATP) into mechanical force and motion. Hence variants or fragments of the molecules can be used, such as myosin I or myosin II, or heavy meromyosin (although light meromyosin would not be suitable because it lacks the heads which change conformation to transduce the chemical energy). Similarly, variant or mutant forms of the motor proteins, such as variant actin or myosin (for example proteins in which conservative amino acid substitutions have been made) are also included, as long as they retain the motor activity. Actin is a directionally oriented molecule, that (when applied directionally to a substrate) helps direct myosin along a substrate in a direction determined by the orientation of the actin molecules on the surface. Actin and myosin have been well studied, and mutations that affect their function have been reported in the scientific literature to provide guidance about making mutants. See, for example, J. Cell. Biol., 134:895-909, 1996; J. Biol. Chem. 269:18773-18780, 1994; and Bioessays 19:561-569, 1997.

The motor proteins may also include kinesin and related proteins, such as ncd, as disclosed in Endow et al., Nature 345:81-83, 1990, that are highly processive, i.e. which do not readily detach from directional microtubule tracks to which they are coupled. Once such highly processive motor proteins attach to a microtubule, there is a relatively high likelihood that they will move for many micrometers along the microtubule before becoming detached. Kinesin moves toward the plus-end of microtubules, whereas ncd moves toward the minus-end of microtubules. Hence, like actin, the microtubules can be applied directionally to a substrate to pre-select a direction of rotation of the surfaces relative to one another. The direction of rotation can be varied, depending on the complementary motor protein which is selected (for example, kinesin or nod).

The motor proteins also include species variations, and various sequence polymorphisms that exist, wherein amino acid substitutions in the protein sequence do not affect the essential functions of the protein.

Coupling of a motor protein to the surfaces of the rotatable cylinders, cones, discs, rings, or loops of the motor can be accomplished by any method known in the art, as long as the motor activity of the protein is preserved. An example of a method of expressing actin as a fusion protein that is then coupled to a substrate is given in Example 4, in which a fusion protein is expressed by recombinant DNA technology. Briefly, a gene encoding a motor protein is operably linked to a gene encoding a selected tag (such as poly-His or streptavidin) to construct a gene fusion, which is then expressed in a suitable expression system such as *E. Coli* or yeast to produce the fusion protein. Coupling of the motor protein to the substrate can also be accomplished by other methods, such as chemical coupling or purified proteins.

Effective amount means an amount of a source of chemical energy, such as ATP, sufficient to permit a selected motor protein to generate mechanical force.

ATP means adenosine triphosphate, a mononucleotide that stores chemical energy that is used by motor proteins, such as myosin and kinesin, for producing movement. ADP refers to adenosine diphosphosphate.

GTP means guanosine 5'-triphosphate, a mononucleotide that stores chemical energy.

cDNA (complementary DNA): a piece of DNA lacking internal, non-coding segments (introns) and regulatory sequences which determine transcription. CDNA is synthesized in the laboratory by reverse transcription from messenger RNA extracted from cells.

Deletion: the removal of a sequence of DNA, the regions on either side being joined together.

Fuel source means a molecule that stores chemical energy. In one embodiment, the energy molecule is a nucleoside triphosphate (NTP), such as ATP or GTP.

Motor protein gene: a gene (DNA sequence) encoding a motor protein (such as actin or myosin). A mutation of the gene (to produce variant forms of the motor protein) may include nucleotide sequence changes, additions or deletions. The term "gene" is understood to include the various sequence polymorphisms and allelic variations that exist within the population. This term relates primarily to an isolated coding sequence, but can also include some or all of the flanking regulatory elements and/or intron sequences.

NTP means a nucleoside 5'-triphosphate, e.g. ATP or GTP.

Isolated: requires that the material be removed from its original environment. For example, a naturally occurring DNA or protein molecule present in a living animal is not isolated, but the same DNA or protein molecule, separated from some or all of the coexisting materials in the natural system, is isolated.

Operably linked: a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

ORF: open reading frame. Contains a series of nucleotide triplets (codons) coding for amino acids without any termination codons. These sequences are usually translatable into protein.

PCR: polymerase chain reaction. Describes a technique in which cycles of denaturation, annealing with primer, and then extension with DNA polymerase are used to amplify the number of copies of a target DNA sequence.

Purified: the term "purified" does not require absolute purity; rather, it is intended as a relative term. Thus, for example, a purified protein preparation is one in which the protein referred to is more pure than the protein in its natural environment within a cell. The term "substantially pure" refers to a purified protein having a purity of at least about 75%, for example 85%, 95% or 98%.

Recombinant: a recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Sequence identity: the similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar are the two sequences.

Methods of alignment of sequences for comparison are well-known in the art. Various programs and alignment algorithms are described in: Smith and Waterman, *Adv. Appl Math.* 2:482, 1981; Needleman and Wunsch, *J. Mol. Bio.* 48:443, 1970; Pearson and Lipman, *Methods in Mol. Biol.* 24: 307-31, 1988; Higgins and Sharp, *Gene* 73:237-44, 1988; Higgins and Sharp, *CABIOS* 5:151-3, 1989; Corpet et al., *Nuc. Acids Res.* 16:10881-90, 1988; Huang et al., *Comp. Appl. Bio Sci.* 8:155-65,1992; and Pearson et al., *Meth. Mol. Biol.* 24:307-31, 1994.

The NCBI Basic Local Alignment Search Tool (BLAST) (Altschul et al., *J. Mol. Biol.* 215:403-10, 1990) is available from several sources, including the National Center for Biological Information (NCBI, Bethesda, Md.) and on the Internet, for use in connection with the sequence analysis programs blastp, blastn, blastx, tblastn and tblastx. It can be accessed at the NCBI web site. A description of how to determine sequence identity using this program is available at the NCBI web site.

Variants or homologs of the motor protein are typically characterized by possession of at least 70% sequence identity counted over the full length alignment with the disclosed amino acid sequence using the NCBI Blast 2.0, gapped blastp set to default parameters. Such homologous peptides will more preferably possess at least 75%, more preferably at least 80% and still more preferably at least 90%, 95% or 98% sequence identity determined by this method. Sequence identity can be determined, in one instance, by aligning sequences and determining how many differences there are in the aligned sequence, and expressing these differences as a percentage. When less than the entire sequence is being compared for sequence identity, homologs will possess at least 75% and more preferably at least 85% and more preferably still at least 90%, 95% or 98% sequence identity over short windows of 10-20 amino acids. Methods for determining sequence identity over sequence windows are described at the NCBI web site. For comparisons of nucleic acid sequences of less than about 150 nucleic acids, the Blast 2 sequences function is employed using the default 0 BLOSUM62 matrix set to default parameters, (OPEN GAP 5, extension gap 2). Nucleic acid sequences with even greater similarity to the reference sequences will show increasing percentage identities when assessed by this method, such as at least 45%, 50%, 70%, 80%, 85%, 90%, 95% or 98% sequence identity.

The present disclosure provides not only the peptide homologs that are described above, but also nucleic acid molecules that encode such homologs.

Transformed: a transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: a nucleic acid molecule is introduced into a host cell, thereby producing a transformed host cell. A vector may include nucleic acid sequences that permit it to replicate in a host cell, such as an origin of replication. A vector may also include one or more selectable marker genes and other genetic elements known in the art.

Particular Embodiments

EXAMPLE 1

A particular embodiment of the molecular motor 10 is illustrated in FIG. 1, in which the motor is shown to include a solid inner cylinder 12 and a hollow outer cylinder 14 that is of slightly larger diameter than inner cylinder 12. An extension 16 of inner cylinder 12 projects from motor 10, and carries a driver in the form of a toothed gear 18. The teeth on gear 18 mesh with the teeth of a larger gear 20, so that rotation of gear 18 in the direction of arrow 22 will rotate gear 20 in the direction of arrow 24.

Although the dimensions of motor 10 are not critical, the inner cylinder 12 may have a diameter of 20 microns to 1 meter, for example 1 cm, while the outer cylinder 14 may have a diameter of 40 microns to 1 meter, for example 1 cm. A clearance distance between an outer surface of cylinder 12 and an inner surface of cylinder 14 is, for example, in the range of 20 to 30 microns.

Referring again to FIG. 1, a layer of actin 30 is directionally applied to the outer surface of cylinder 12, with the directional orientation shown as arrows in the drawing. As described in greater detail in Example 4, the actin protein may be expressed with a histidine tag (for example His-6) that binds to nickel. The actin is polymerized to form actin fibers by bringing a $Mg^{2+}$ concentration to physiological levels, as described in Korn et al., *Science* 238:638-644, 1987. A cylinder with a nickel outer surface is placed into the actin-His-6 fiber solution so that the fibers attach to the surface of the cylinder. The cylinder may then be placed in a normal (non-His-6) actin solution (for example by adding normal actin to the solution) to extend the actin fibers to a length beyond their persistence length (at which point the actin has no particular direction). More actin-His-6 is then added to the solution, so that the ends of the actin cables have a His tag, and the cylinder is rotated in the actin solution to directionally orient the actin cables, and allow the His tags at the free end of the actin cables to attach to the nickel containing surface of the cylinder 12.

The directionality of the actin cables is schematically illustrated in FIG. 1 by arrows 32 in the actin layer 30. As shown by the cut away portion of cylinder 14 in FIG. 1, the coating of actin covers the curved surface of inner cylinder 12 substantially along its length, for substantially coating that surface of the cylinder. In particular embodiments, the actin is present in a substantially continuous layer around the circumference of the cylinder 12, for substantially the entire length of the cylinder inside outer cylinder 14. The thickness of the actin layer may be, for example, 1 to 10 molecules thick, and in a particular disclosed embodiment is one molecule thick.

The myosin (for example in the form of myosin I, myosin II, or heavy meromyosin, or variants thereof) can be adhered to the inner surface of cylinder 14, before actin coated cylinder 12 is placed inside cylinder 14. The myosin is adhered to the inner surface of cylinder 14 by adhesion, or by the techniques shown in Finer et al., Nature 368:113-119, 1994, and Ishijima et al., Cell 92:161-171, 1998, as well as Ishijima et al, Biophys. J. 70:383-400, 1996 (incorporated by reference), in which myosin was purified and bound to a glass surface. When heavy meromyosin (HMM) is used as the motor protein, the technique used in Suzuki et al., Biophys. J. 72:1997-2001, 1997 (incorporated by reference) can be used. In this method, HMM (0.1 mg/ml) in an assay buffer solution (40 mM KCl, 3 mM MgCl2, 2mM EGTA, 10 mM dithiothreitol, and 20 mM HEPES at pH 7.8) is dropped on to a polymethylmethacrylate (PMMA) substrate, and the HMM is adsorbed. PMMA is a useful substrate, because photolithographic patterns can be made in them, if desired, and the HMM placed into the tracks. In FIG. 1, the myosin is schematically shown as myosin heads 34 projecting from the inner surface of cylinder 14.

Once the myosin has been adhered to the inner surface of cylinder 14, cylinder 12 may be inserted inside cylinder 14, with both cylinders arranged concentrically around a common longitudinal axis 36. External cylinder 14 may be mounted to a stationary surface 38 by a bracket 40, so that the cylinder 14 remains fixed, and inner cylinder 12 is free to rotate relative to cylinder 14, around the central longitudinal axis 36.

In operation, a solution that contains an effective concentration of ATP is introduced into the flow space 42 between cylinders 12, 14, and allowed to flow through the cylinders along their entire length. Particular concentrations of ATP (Sigma Chemical Co., St. Louis, Mo.) that can be supplied are solutions with an ATP concentration of 0.1 to 1000 µM, for example 1 µM. Greater concentrations of ATP would activate more of the myosin molecules, and increase the speed of the motor, by rotating cylinder 12 relative to cylinder 14. As cylinder 12 rotates, extension 16 rotates gear 18 in the direction of arrow 22, which in turn rotates gear 20 in the direction of arrow 24. The molecular mechanism by which this rotation is achieved is described in more detail in Example 2.

An alternative embodiment is shown in FIG. 2, which is similar to that shown in FIG. 1, such that like parts have been given like reference numbers plus 100. However, instead of inner and outer cylinders, the motor includes inner and outer frusto-cones 112, 114 (which for simplicity will be referred to as "cones" 112, 114). FIG. 2 shows the molecular motor 110 in which the outer cone 114 is mounted to a bracket 140 and surface 138. Outer cone 114 is positioned around inner cone 112, such that the cones taper in a complementary fashion, from a large diameter base to a smaller diameter tip, and rotate around a common longitudinal axis of rotation 136. A layer of actin 130 is directionally attached to the outer surface of inner cone 112, while myosin 134 is adhered to the inner surface of outer cone 114. When supplied with fuel, inner cone 112 rotates extension 116 and driving gear 118 in the direction of arrow 122, which in turn rotates driven gear 120 in the direction or arrow 124.

An advantage of the embodiment of FIG. 2 is that the motor can be assembled by inserting inner cone 112 inside outer cone 114, with less shearing force than may be encountered when introducing an inner cylinder into a larger outer cylinder. Since the smaller diameter top portion of the tapering inner cone 112 can be introduced into the larger diameter base opening of the outer tapering cone 114, there is a greater clearance between the inserted end and the surrounding cone than would occur with two cylinders, each of which has a constant radius. As the inner cone 112 is progressively inserted into the outer cone 114, the minimum desired operational clearance between the actin and myosin layers is not reached until the two cones reach their final operational positions. Hence the opportunity for shearing of the actin and myosin layers, by frictional forces encountered as the motor is assembled, is minimized.

Figure 3B:
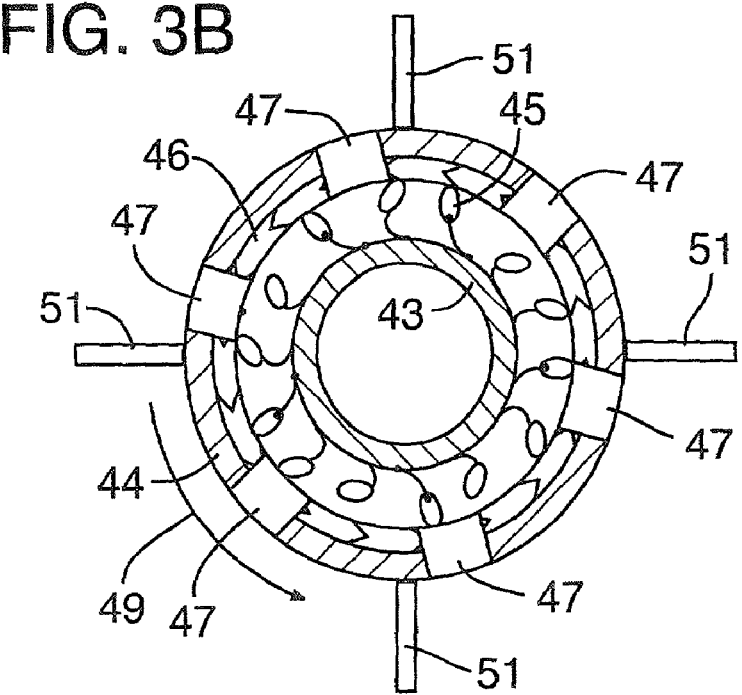

Another alternative embodiment of the motor is shown in FIGS. 3A and 3B, in which a hollow inner cylinder 43 is surrounded by an outer cylinder 44. Myosin 45 (with the heads shown in random states of conformational change in FIG. 3B) is coated on an external surface of inner cylinder 43, while a layer of actin 46 is directionally applied to an inner surface of outer cylinder 44. Openings 47 are arrayed circumferentially around outer cylinder 44, and provide passageways through the cylinder 44 and actin layer 46, through which an ATP containing liquid can be introduced into the space between cylinders 43 and 44. Inner cylinder 43 extends beyond an open end of outer cylinder 44, and is mounted on a stationary bracket 48. Myosin need not be coated on the outer surface of cylinder 43 which extends out of cylinder 44.

In operation, a liquid containing a sufficient concentration of ATP is introduced through passageways 47, for example through manifold tubes (not shown) which communicate with the passageways. In the presence of the ATP, the myosin heads 45 undergo a conformational change to attach to actin layer 46 and move it in the direction indicated by arrow 49. As the actin layer is moved, its attached outer cylinder 44 is rotated around its longitudinal axis in the direction 49, which in turn rotates propeller blades 51 that extend outwardly from the outer surface of cylinder 44. The rotation of blades 51 can be converted to useful work, such as the generation of power.

Although FIGS. 3A and 3B show perforations 47 in the external cylinder 44 for introducing liquid fuel into the motor, the liquid could similarly be introduced into the interior of the hollow inner cylinder 43. Perforations in cylinder 43 could be provided to direct the flow of liquid out of the inner cylinder, and this flow would be encouraged by rotation of the surrounding outer cylinder 44.

The molecular motor can be used in a biological organism, such as a mammal, for example to move limbs or other body parts that may have lost neuromuscular activity. When used to move a limb, for example, the rotation of outer cylinder 44 can be used to rotate a joint, for example to perform pronation or supination of the forearm. In an assembly such as that shown in FIGS. 3A and 3B, the inner cylinder can be fixed axially to a bone (such as the radius or ulna, or both), and the rotating outer cylinder can be fixed to the humerus. Activation of the motor would then rotate the forearm relative to the upper arm. In such an example, a motor with multiple layers would likely be required to provide sufficient power to rotate a joint.

In yet other applications, the molecular motor may be used in a robot, for example to rotate joints of the extremities or trunk. Rotation of the motor can also be used in a pump to propel fluids. Very large versions of the motor (such as multiple cylinder embodiments about one meter wide) could also be used in automobiles to replace conventional internal combustion motors.

EXAMPLE 2

Movement of Substrates by Conformational Change of Myosin Heads

The molecular mechanism by which conformational changes of the myosin heads move an actin coated substrate are illustrated in FIGS. 4 and 5, which depict a conventional version of the mechanism of muscle contraction. Although this version is illustrated for purposes of explanation and illustration, the disclosure is not limited to this theory, and covers any actual mechanism of muscle contraction eventually discovered.

FIG. 4 shows a flat substrate 200 coated with a directionally oriented layer of actin 202. In FIG. 4A, the myosin head 204 is shown at the end of a power stroke which has moved substrate 200. In step 1 between FIG. 4A and FIG. 4B, ATP binds to the myosin head 204, which causes release of the myosin head 204 from the actin 202. ATP is then rapidly hydrolyzed, leaving ADP and inorganic phosphate ($P_i$) bound to the myosin 204, and resulting in a conformational change (FIG. 4C) in the shape of the myosin head which moves the head backward with respect to the direction of desired movement of the actin. This change is followed by the myosin binding to actin in a high energy state (FIG. 4D). The ADP-Pi is then released, which results in another conformational change that moves the myosin in the direction of arrow 206, and drives the actin filament by a distance of between 4 and 10 mn in that direction.

A similar proposed mechanism applies to the movement of a curved substrate, such as the cylinder 212 (FIG. 5) which is coated with the layer of actin 230. FIG. 5A shows the myosin heads 234 at the end of a power stroke. Although several myosin heads are shown in FIG. 5 undergoing uniform movements, the myosin head which are shown are only a subset of myosin molecules that are undergoing similar conformational changes. Although not shown in the drawing, many other myosin molecules are simultaneously in different stages of the cycle.

In step 1, between FIGS. 5A and 5B, ATP binds to the myosin heads 234, which causes release of the heads from the directionally oriented actin layer 230. The ATP is subsequently hydrolyzed in step 2, leaving ADP and Pi (illustrated as a black spot on the myosin head in FIG. 5C), and resulting in a conformational change that moves the myosin head in a direction opposite the direction of movement of the directionally oriented actin. The myosin heads then attach to the actin fibers (FIG. 5D), and the ADP-Pi is released, resulting in a conformational change of the myosin that drives the heads in the direction of arrow 236. This movement in turn moves the actin in the direction of arrow 236 to turn the inner cylinder, and power the motor.

EXAMPLE 3

Multiple Concentric Cylinders to Increase Speed of Motor

Figure 6:
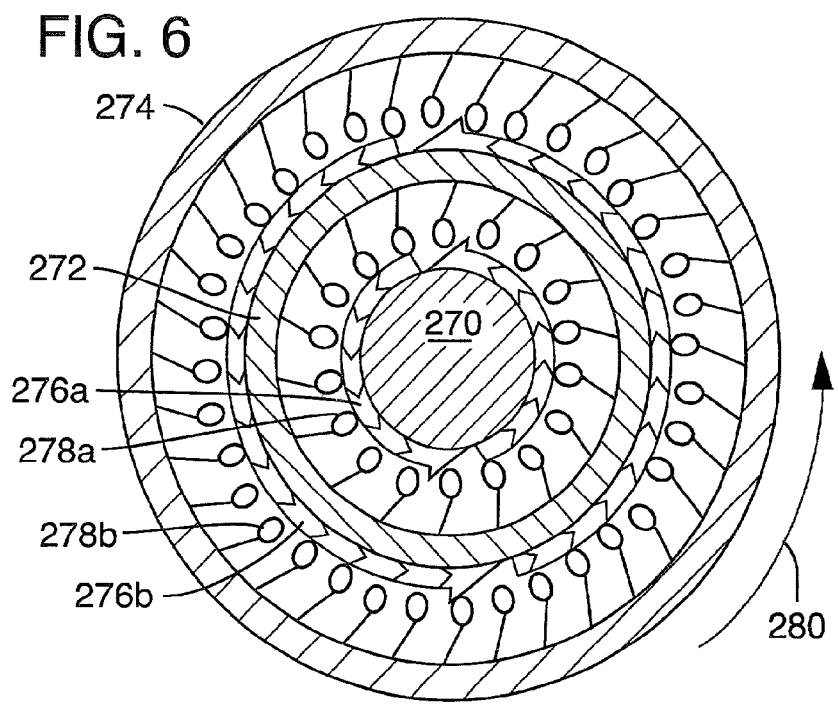
FIG. 6 is a schematic side view of an alternative embodiment of the motor having multiple, nested, concentric complementary cylinders on which the actin and myosin are coated.

Another embodiment of the motor is shown in FIG. 6, in which multiple concentric cylinders are used to construct a motor that can rotate at a higher speed than a motor having only an inner and an outer cylinder. In the embodiment of FIG. 6, the motor includes a solid inner cylinder 270, an intermediate cylinder 272, and an outer cylinder 274. Although three cylinders are shown in this example, a motor containing many more cylinders (for example 5, 10, 25, 50 or even more concentric cylinders) can similarly be used.

The construction of the motor in FIG. 6 is analogous to that shown in FIGS. 1-3, in that opposing surfaces of the cylinders are coated with complementary pairs of motor proteins, such as actin and myosin. Hence inner cylinder 270 has a layer of actin 276a directionally coated on its external surface, while intermediate cylinder 272 has a coating of myosin 278a on its inner surface. Intermediate cylinder 272 also has a directional layer of actin 276b on its outer surface, and outer cylinder 274 has a coating of myosin 278b on its inner surface.

In operation, the outer cylinder 274 is held stationary, for example by a bracket. When an ATP-containing liquid is introduced into the spaces between the three cylinders, the myosin on the inner surface of outer cylinder 274 moves intermediate cylinder 272 in the direction indicated by arrow 280. Simultaneously the inner cylinder 270 is rotated in the direction of arrow 280 by the interaction of the complementary actin and myosin layers on the cylinders 270, 272. Hence the rotational speed of inner cylinder 270 is the sum of the rotational speeds of intermediate cylinder 272 and inner cylinder 270. By using even more concentric cylinders that rotate about a common longitudinal axis, the rotational speed on the inner cylinder can be increased correspondingly.

Alternatively, in embodiments such as that shown in FIGS. 3A and 3B in which the outer cylinder rotates relative to a stationary inner cylinder, multiple concentric cylinders in the motor would increase the rotational speed of the external cylinder.

Figure 7A:
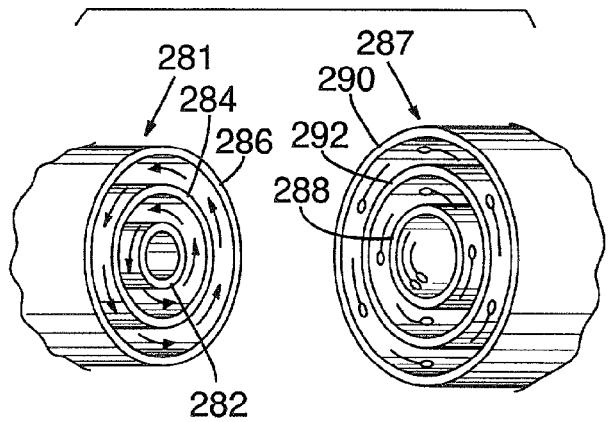
FIG. 7A is a schematic end perspective view of two interengaging complementary cylinders that can be interengaged to assemble a molecular motor of the present disclosure.
Figure 7B:
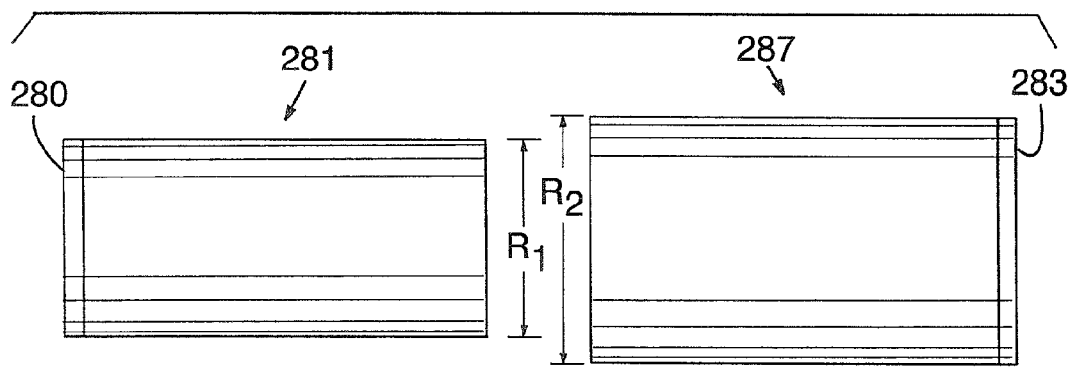
FIG. 7B is a side view of the complementary cylinders of FIG. 4, illustrating the differing outer diameters of the two cylinders.

FIGS. 7A and 7B illustrate a particular mode of assembly of molecular motors that have multiple concentric nested cylinders. A first set 281 of hollow coaxial cylinders is held in the concentric array shown in FIG. 7A, for example by a series of internal struts, or by affixation of an external end plate 280 (FIG. 7B) at a closed end of the array. Set 281 includes three hollow coaxial cylinders, consisting of an inner cylinder 282, and intermediate cylinder 284, and an outer cylinder 286. A second set 287 of coaxial cylinders is similarly held in a concentric array by internal struts, or affixation of an external end plate 283 at a closed end of the array (FIG. 7B). Set 287 also includes three cylinders, consisting of an inner cylinder 288, an intermediate cylinder 292, and an outer cylinder 290.

The overall outer diameter R1 of set 281 is slightly less than an overall outer diameter R2 of set 287, and the corresponding arrays of the alternate sets 281, 287 have staggered diameters from the innermost to the outermost cylinder. Hence the outer diameter of cylinder 282 is slightly less than the inner diameter of cylinder 288. Similarly, the outer diameter of cylinder 288 is slightly less than the inner diameter of cylinder 284, and the outer diameter of cylinder 284 is slightly less than the inner diameter of cylinder 292.

As illustrated schematically in FIG. 7A, actin is directionally applied to the outer surfaces of both of the cylinders 282, 284 (where the directional application of the actin is illustrated by the direction of the arrows on the outer surfaces of those cylinders). Myosin is applied to the inner surfaces of cylinders 288, 290 and 292. Hence the motor can be assembled by introducing set 281 into set 287, so that the cylinders of set 281 interdigitate with the cylinders of set 287. Once assembled, the motor can be operated by introducing an ATP containing liquid into the spaces between the cylinders.

In another embodiment (not shown), each actin bearing surface can have raised circumferential ridges longitudinally spaced along it. Such raised ridges would provide areas of reduced clearance between the inner and outer cylinders, to increase the interaction between the cylinders.

Figure 8:
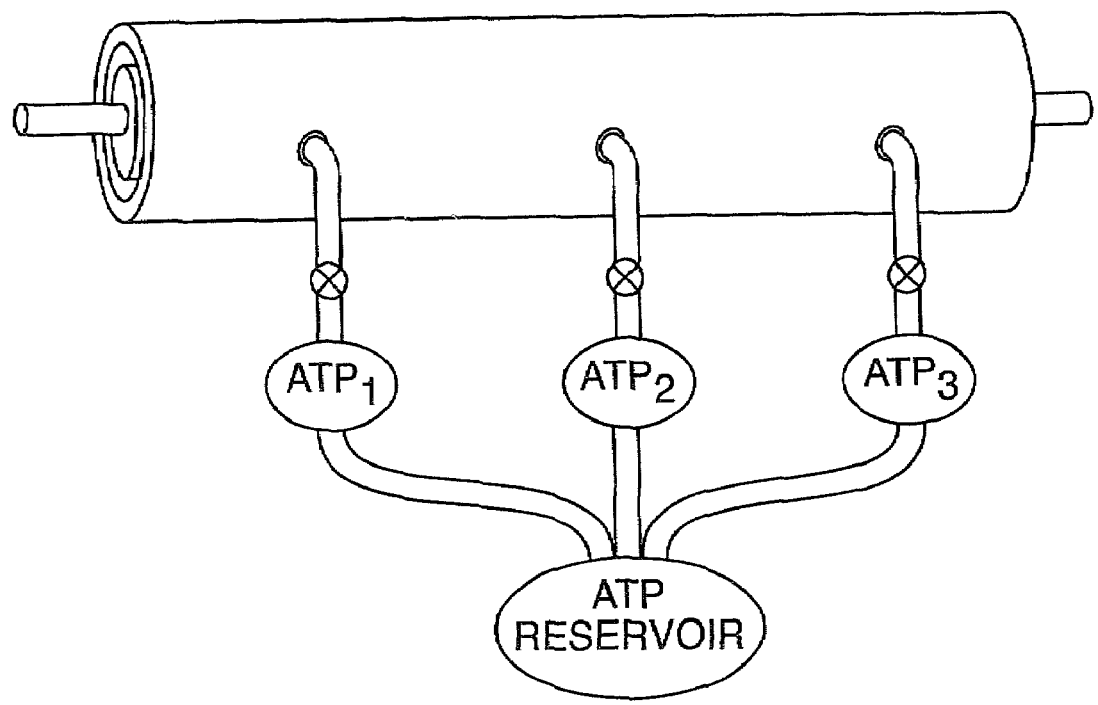
FIG. 8 is a schematic illustration of one embodiment of the molecular motor, in which ATP is supplied from a reservoir. Separate feed lines are used to supply the ATP to the motor. Each feed line ($ATP_1$, $ATP_2$, and $ATP_3$) has a control switch or valve (designated "X" on the $ATP_1$, $ATP_2$, and $ATP_3$ feed lines). In one embodiment, the control valves are separately controlled.

When a set number of concentric nested cylinders is included in a molecular motor, the motor operates at a defined maximum power and speed. However, it may be desirable to be able to vary the power of the motor. As shown in FIG. 8, the molecular motor may be elongated along the horizontal axis. The fuel source (e.g., an energy molecule such as a nucleotide triphosphate, NTP) is provided from a reservoir. In one embodiment, the fuel source is ATP.

The fuel source is selected based on the enzyme system of the molecular motor. For example, if helicases and DNA strands are included in a molecular motor, NTPs are provided in the reservoir (see Waksman et al., Nat. Struct. Biol. 7:20-22, 2000 for a discussion of helicases). In another specific, non-limiting example, actin and myosin are included in the molecular motor, and ATP is provided as the fuel source in the reservoir.

The fuel source (e.g. ATP) is supplied to the molecular motor by feed lines (designated $ATP_1$, $ATP_2$, $ATP_3$) that are controlled by switches or valves (designated X on feed lines $ATP_1$, $ATP_2$, $ATP_3$) that regulate the flow rate of fuel (e.g. ATP) through the feed lines. Power is varied by changing the amount of available fuel along the length of the motor using the control switches or valves.

In the embodiment illustrated, there are three feed lines and switches, however, any number of independently controlled feed lines and switches can be utilized. The control switches or valves can be regulated individually, regulated in groups (e.g. 2, 3, or 4 valves that are regulated together), or can be regulated as a single unit.

Thus, in one specific, non-limiting example, independently controlled switches are utilized to control the flow of ATP through the feed lines. If three switches and three ATP feed lines are connected to the motor, switching one of the three independently controlled switches off decreases the power to two-thirds of the maximal power.

Figure 9:
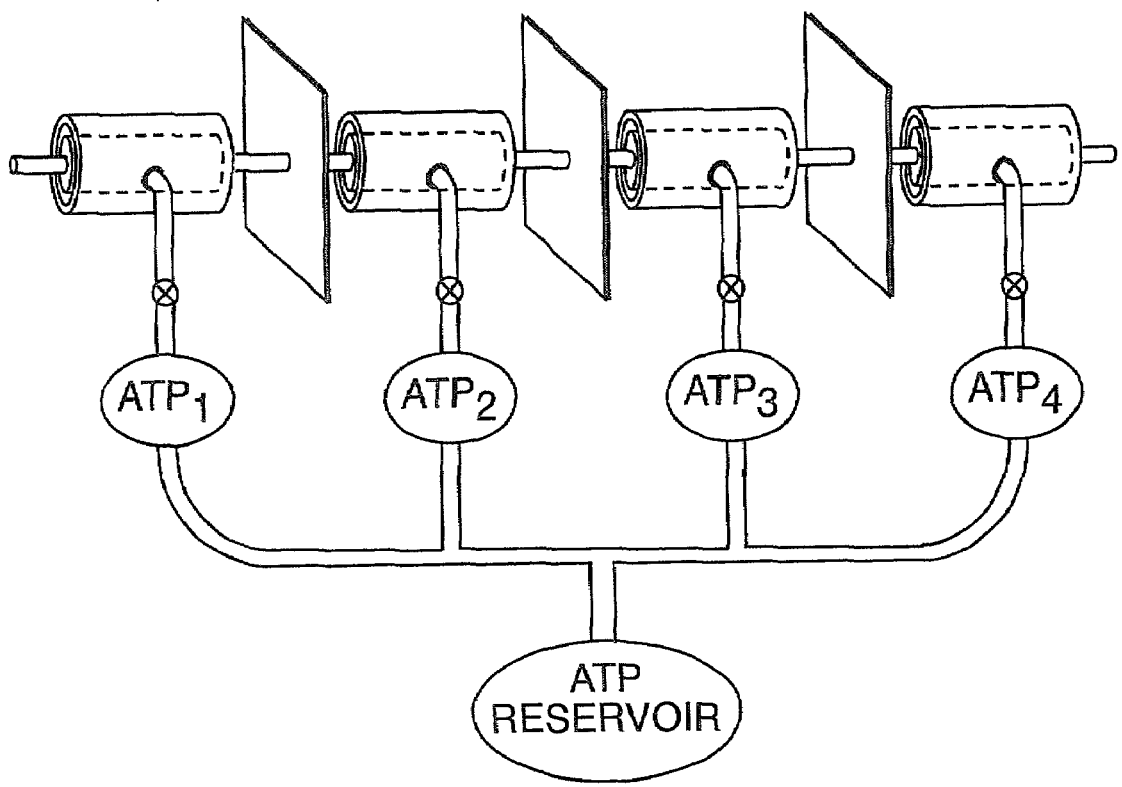
FIG. 9 is a schematic illustration of another embodiment of the molecular motor, which includes separate units in series. In this embodiment, segments of a molecular motor, separated by impermeable barriers, are connected in series by a shaft. The barrier is designed to prevent diffusion between the molecular motor units. In this embodiment, ATP is supplied from a reservoir through separate feed lines (designated $ATP_1$, $ATP_2$, $ATP_3$ and $ATP_4$). Each feed line ($ATP_1$, $ATP_2$, $ATP_3$ and $ATP_4$) has a separately controlled switch or valve (designated "X" on $ATP_1$, $ATP_2$, $ATP_3$ and $ATP_4$ feed lines).

Another embodiment of the molecular motor, wherein power can be regulated, is shown in FIG. 9. In this embodiment, independent segments of a molecular motor are provided. Each segment of the motor (shown as an independent cylinder) is attached to one end of a feed line (designated $ATP_1$, $ATP_2$, $ATP_3$ and $ATP_4$). The other end of each feed line is connected to a fuel source (e.g. ATP) in a reservoir, which can deliver the fuel through the feed lines to the segments of the molecular motor. In the embodiment shown, the flow of ATP from the reservoir through the feed lines is controlled by valves or switches (designated "X" on each feed line). The motor segments are separated by impermeable barriers (shown schematically as squares) that prevent, or substantially inhibit, diffusion between the motor segments.

In the embodiment illustrated, four feed lines and switches are shown, however, any number of independently controlled feed lines and switches can be utilized. Moreover, each of the segments can have multiple supply lines (as in FIG. 8). The control switches or valves shown in FIG. 9 can be regulated individually, regulated in groups (e.g. 2, 3, or 4 valves that are regulated together), or can be regulated as a single unit.

In one specific, non-limiting example, segments of the motor are powered independently to avoid shear. For example, if the segments are numbered sequentially, the switch can be used to prevent delivery of ATP to every other segment (e.g. the odd segments) in order to run the molecular motor at half of the maximum power. Similarly, the switch can be used to prevent delivery of ATP to every third segment (e.g. those with a multiple of three) to run the molecular motor at two-thirds power. The switch can also be used to prevent delivery of ATP to two out of three segments to run the molecular motor at one-third power.

The segments of the motor can all be of the same length, or can have different lengths. Altering the lengths of the segments allows variations in power. In addition, altering the numbers of nested cylinders allows the velocity to be varied. Thus, a range of controls is provided.

In one embodiment, a series in which the first segment has a unit length of 1, a second segment has a unit of length 2, and third segment has a unit of length of 4, and a fourth segment has a unit length of 8 is provided. This series can, by binary combinations, be programmed to have from 0 to 15 units of power. One of skill of the art will be able to determine an appropriate switching paradigm of segments of molecular motor of various lengths such that any desired fraction of the maximal power of the molecular motor can be achieved.

EXAMPLE 4

Preparation of Recombinant Actin

This example describes how to prepare recombinant actin molecules, which may also contain at least one affinity tag. Such tags serve as a means by which to attach actin to a substrate, and aid in the purification of recombinant actin. Purified recombinant actin may be used for the molecular motor of the present disclosure.

Standard molecular biology protocols are used for the expression and purification of recombinant actin unless otherwise stated. Such methods are described, for example, in Sambrook et al. (*Molecular Cloning: A Laboratory Manual*, Cold Spring Harbor, N.Y., 1989), Ausubel et al. (*Current Protocols in Molecular Biology*, Greene Publishing Associates and Wiley-Intersciences, 1987), and Innis et al., (*PCR Protocols, A Guide to Methods and Applications*, Innis et al. (eds.), Academic Press, Inc., San Diego, Calif., 1990).

Partial or full-length cDNA sequences, which encode for actin, may be ligated into bacterial expression vectors. The actin cDNA can be from any organism including human, chicken or mouse, and includes wild-type, mutant, and sequence variants thereof In addition, the actin cDNA may be from any isotype of actin, including the α, β, and γ isoforms. Any sequence variants used in the present disclosure will retain the ability to interact with myosin so that the myosin can move the actin, as in muscle. Several actin cDNA sequences are publicly available on GenBank at: http://www.ncbi.nlm.nih.gov/Entrez/. Examples include the human (Accession No. J0068) and chicken (Accession Nos. V01507 J00805 K02172 K02257) α-actin genes, the mouse β-actin gene (Accession No. XO3672), and the human γ-actin gene (Accession Nos. X04098, K00791, M24241). It is appreciated that for mutant or variant DNA sequences, similar systems as described below are employed to express and produce the mutant or variant product.

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate, or with the use of specific oligonucleotides in combination with PCR.

The host cell, which may be transfected with the vector of this disclosure, may be selected from the group consisting of bacteria, yeast, fungi, plant, insect, mouse or other animal, or human tissue cells.

The purification of recombinant fusion proteins has been made significantly easier by the use of affinity tags that can be genetically engineered at either the N- or C-terminus of recombinant proteins. Such tags can be attached to actin, to aid in its purification and subsequent attachment to a substrate (see Example 1). Examples of affinity tags include histidine (His), streptavidin, S-tag, and glutathione-S-transferase (GST). Other affinity tags known to those skilled in the art may also be used.

In general, the affinity tags are placed at the N- or C-terminus of a protein. Vectors containing one or multiple affinity tags are commercially available. To prepare a Tag-actin recombinant fusion protein, vectors are constructed which contain nucleotide sequences encoding the tag, and the actin cDNA. This vector may be expressed in bacteria such as *E. coli*, and the protein purified. The method of purification will depend on the affinity tag attached. Typically, the bacterial lysate is applied to a column containing a resin having high affinity for the tag on the fusion protein. After applying the lysate and allowing the tagged-fusion protein to bind, unbound proteins (non-tagged) are washed away, and the fusion protein (containing the affinity tag) is eluted.

One of the most widely used tags contains six or ten consecutive histidine (His) residues, which has high affinity for metal ions (such as nickel ion) which can be placed on a surface of a curved substrate to which the actin is to be attached. A His-6 or His-10 moiety can be attached to actin using pET vectors (Novagen, Madison, Wis.). The His-actin fusion protein can be purified as described in Paborsky et al. (*Anal. Biochem.*, 234:60-65, 1996), herein incorporated by reference. Briefly, the cell lysate is immobilized by affinity chromatography on $Ni^{2+}$-NTA-Agarose (QIAGEN, Valencia, Cailf.). After washing away unbound proteins, for example using a buffer containing 8-50 mM imidazole, 50 mM Tris HCl, pH 7.5, 150 mM NaCl, the bound recombinant protein is eluted using the same buffer containing a higher concentration of imidazole, for example 100-500 mM imidizole.

The S-tag system is based on the interaction of the 15 amino acid S-tag peptide with the S-protein derived from pancreatic ribonuclease A. Several vectors for generating S-tag fusion proteins, as well as kits for the purification of S-tagged proteins, are available from Novagen (Madison, Wis.). For example vectors pET29a-c and pET30a-c can be used. The S-tag-actin fusion protein may be purified by incubating the cell lystae with S-protein agarose, which retains S-tag-actin fusion proteins. After washing away unbound proteins, the fusion protein is released by incubation of the agarose beads with site-specific protease, which leaves behind the S-tag peptide. The S-tagged protein can then be attached to the cylinder substrate, for example by the His tag provided by this vector on the C terminus.

The affinity tag streptavidin binds with very high affinity to biotin. Vectors for generating streptavidin-actin fusion proteins, and methods for purifying these proteins, are described in Santo and Cantor (*Biochem. Biophys. Res. Commun.* 176:571-577, 1991, herein incorporated by reference). To purify the streptavidin-actin fusion protein, the cell lysate is applied to a 2-iminobiotin agarose column (other biotin-containing columns may be used), and after washing away unbound proteins, the fusion protein is eluted. Biotin can be attached to the substrate (a surface of the cylinder, such as a glass cylinder) using the techniques disclosed by Mazzola and Fodor, Biophys. J. 68:1653-1660, 1995, which is incorporated by reference.

The enzyme glutathione-S-transferase (GST) has high affinity for glutathione. Plasmid expression vectors containing GST (PGEX) are disclosed in U.S. Pat. No. 5,654,176 to Smith, herein incorporated by reference and in Sharrocks (*Gene,* 138:105-8, 1994, herein incorporated by reference). pGEX vectors are available from Amersham Pharmacia Biotech (Piscataway, N.J.). The cell lysate is incubated with glutathione-agarose beads and after washing, the fusion protein is eluted, for example, with 50 mM Tris-HCl (pH 8.0) containing 5 mM reduced glutathione. If the GST-fusion protein is insoluble, it can be purified by affinity chromatography if the protein is solubilized in a solubilizing agent which does not disrupt binding to glutathione-agarose, such as 1% Triton X-100, 1% Tween 20, 10 mM dithiothreitol or 0.03% $NaDodSO_4$. Other methods used to solubilize GST-fusion proteins are described by Frangioni and Neel (*Anal. Biochem.* 210:179-87, 1993, herein incorporated by reference). Glutathione fusion proteins can be attached to an agarose covered substrate, for example a layer of agarose on the cylindrical substrate, for example by using the techniques disclosed in Lewis et al., Protein Expr. Pruif. 13:120-126, 1998, which is incorporated by reference.

Methods and plasmid vectors for producing fusion proteins and intact native proteins in bacteria are described in Sambrook et al. (*Molecular Cloning: A Laboratory Manual,* Cold Spring Harbor, N.Y., 1989, chapter 17, herein incorporated by reference). Such recombinant fusion proteins may be made in large amounts, and are easy to purify. Native proteins can be produced in bacteria by placing a strong, regulated promoter and an efficient ribosome binding site upstream of the cloned gene. If low levels of protein are produced, additional steps may be taken to increase protein production; if high levels of protein are produced, purification is relatively easy. Suitable methods are presented in Sambrook et al. (*Molecular Cloning: A Laboratory Manual,* Cold Spring Harbor, N.Y., 1989) and are well known in the art. Often, proteins expressed at high levels are found in insoluble inclusion bodies. Methods for extracting proteins from these aggregates are described by Sambrook et al. (*Molecular Cloning: A Laboratory Manual,* Cold Spring Harbor, N.Y., Chapter 17, 1989).

Vector systems suitable for the expression of actin fusion genes include the pUR series of vectors (Ruther and Muller-Hill, *EMBO J.* 2:1791, 1983), pEX1-3 (Stanley and Luzio, *EMBO J.* 3:1429, 1984) and pMR100 (Gray et al., *Proc. Natl. Acad. Sci. USA* 79:6598, 1982). Vectors suitable for the production of intact native proteins include pKC30 (Shimatake and Rosenberg, *Nature* 292:128, 1981), pKK177-3 (Amann and Brosius, *Gene* 40:183, 1985) and pET-3 (Studiar and Moffatt, *J. Mol. Biol.* 189:113, 1986). Actin fusion proteins may be isolated from protein gels, for use in the molecular motor. The DNA sequence can also be transferred to other cloning vehicles, such as other plasmids, bacteriophages, cosmids, animal viruses and yeast artificial chromosomes (YACs) (Burke et al., *Science* 236:806-812, 1987). These vectors may then be introduced into a variety of hosts including somatic cells, and simple or complex organisms, such as bacteria, fungi (Timberlake and Marshall, *Science* 244:1313-1317, 1989), invertebrates, plants (Gasser and Fraley, *Science* 244:1293, 1989), and mammals (Pursel et al., *Science* 244:1281-1288, 1989), which cell or organisms are rendered transgenic by the introduction of the heterologous actin cDNA.

For expression in mammalian cells, the actin cDNA sequence may be ligated to heterologous promoters, such as the simian virus SV40 promoter, in the pSV2 vector (Mulligan and Berg, *Proc. Natl. Acad. Sci. USA* 78:2072-2076, 1981), and introduced into cells, such as monkey COS-1 cells (Gluzman, *Cell* 23:175-82, 1981), to achieve transient or long-term expression. The stable integration of the chimeric gene construct may be maintained in mammalian cells by biochemical selection, such as neomycin (Southern and Berg, *J. Mol. Appl. Genet.* 1:327-41, 1982) and mycophoenolic acid (Mulligan and Berg, *Proc. Natl. Acad. Sci. USA* 78:2072-2076, 1981).

The cDNA sequence (or portions derived from it) or a mini gene (a cDNA with an intron and its own promoter) may be introduced into eukaryotic expression vectors by conventional techniques. These vectors are designed to permit the transcription of the cDNA eukaryotic cells by providing regulatory sequences that initiate and enhance the transcription of the cDNA and ensure its proper splicing and polyadenylation. Vectors containing the promoter and enhancer regions of the SV40 or long terminal repeat (LTR) of the Rous Sarcoma virus and polyadenylation and splicing signal from SV40 are readily available (Mulligan and Berg, *Proc. Natl. Acad. Sci. USA* 78:2072-2076, 1981; Gorman et al., *Proc. Natl. Acad. Sci USA* 78:6777-6781, 1982). The level of expression of the cDNA can be manipulated with this type of vector, either by using promoters that have different activities (for example, the baculovirus pAC373 can express cDNAs at high levels in *S. frugiperda* cells (Summers and Smith, *Genetically Altered Viruses and the Environment,* Fields et al. (Eds.) 22:319-328, Cold Spring Harbor Laboratory Press, Cold Spring Harbor, N.Y., 1985) or by using vectors that contain promoters amenable to modulation, for example, the glucocorticoid-responsive promoter from the mouse mammary tumor virus (Lee et al., *Nature* 294:228, 1982). The expression of the actin cDNA can be monitored in the recipient cells 24 to 72 hours after introduction (transient expression).

In addition, some vectors contain selectable markers such as the gpt (Mulligan and Berg, *Proc. Natl. Acad. Sci. USA* 78:2072-6, 1981) or neo (Southern and Berg, *J. Mol. Appl. Genet.* 1:327-41, 1982) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses such as papilloma (Sarver et al., *Mol. Cell Biol.* 1:486, 1981) or Epstein-Barr (Sugden et al., *Mol. Cell Biol.* 5:410, 1985). Alternatively, one can also produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product (Alt et al., *J. Biol. Chem.* 253:1357, 1978).

The transfer of DNA into eukaryotic, in particular human or other mammalian cells, is now a conventional technique. The vectors are introduced into the recipient cells as pure DNA (transfection) by, for example, precipitation with calcium phosphate (Graham and vander Eb, *Virology* 52:466, 1973) or strontium phosphate (Brash et al., *Mol. Cell Biol.* 7:2013, 1987), electroporation (Neumann et al., *EMBO J.* 1:841, 1982), lipofection (Felgner et al., *Proc. Natl. Acad. Sci. USA.* 84:7413-7417, 1987), DEAE dextran (McCuthan et al., *J. Natl Cancer Inst.* 41:351, 1968), microinjection (Mueller et al., *Cell* 15:579, 1978), protoplast fusion (Schafner, *Proc. Natl. Acad. Sci. USA* 77:2163-7, 1980), or pellet guns (Klein et al., *Nature* 327:70, 1987). Alternatively, the cDNA can be introduced by infection with virus vectors. Systems are developed that use, for example, retroviruses (Bernstein et al., *Gen. Engrg.* 7:235, 1985), adenoviruses (Ahmad et al., *J. Virol.* 57:267, 1986), or Herpes virus (Spaete et al., *Cell* 30:295, 1982).

Using the above techniques, the expression vectors containing the actin gene or cDNA sequence or fragments or variants or mutants thereof can be introduced into human cells, mammalian cells from other species or non-mammalian cells as desired. For example, monkey COS cells (Gluzman, *Cell* 23:175-82, 1981) that produce high levels of the SV40 T antigen and permit the replication of vectors containing the SV40 origin of replication may be used. Similarly, Chinese hamster ovary (CHO), mouse NIH 3T3 fibroblasts or human fibroblasts or lymphoblasts may be used.

The recombinant cloning vector, according to this disclosure, then comprises the selected DNA of the DNA sequences of this disclosure for expression in a suitable host. The DNA is operatively linked in the vector to an expression control sequence in the recombinant DNA molecule so that the actin polypeptide can be expressed. The expression control sequence may be selected from the group consisting of sequences that control the expression of genes of prokaryotic or eukaryotic cells and their viruses and combinations thereof. The expression control sequence may be specifically selected from the group consisting of the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

EXAMPLE 5

Motor Protein Variants

Variants of the motor proteins (such as actin and myosin) can be used instead of the native proteins, as long as the variants retain the motor activity. DNA mutagenesis techniques may be used to produce variant DNA molecules, and will facilitate the production of proteins which differ in certain structural aspects from the native protein, yet the variant proteins are clearly derivative and maintain the essential functional characteristic of the motor protein as defined above. Newly derived proteins may also be selected in order to obtain variations in the characteristics of the motor protein, as will be more fully described below. Such derivatives include those with variations in the amino acid sequence including minor deletions, additions and substitutions.

While the site for introducing an amino acid sequence variation is predetermined, the mutation per se need not be predetermined. For example, in order to optimize the performance of a mutation at a given site, random mutagenesis may be conducted at a target codon or region and the expressed protein variants screened for optimal activity. Techniques for making substitution mutations at predetermined sites in DNA having a known sequence are well known.

Amino acid substitutions are typically of single residues, for example 1, 2, 3, 4 or more substitutions; insertions usually will be on the order of about from 1 to 10 amino acid residues; and deletions will range about from 1 to 30 residues. Substitutions, deletions, insertions or any combination thereof may be combined to arrive at a final construct. Obviously, the mutations that are made in the DNA encoding the protein must not place the sequence out of reading frame, and preferably will not create complementary regions that could produce secondary changes in the mRNA structure.

Substitutional variants are those in which at least one residue in the amino acid sequence has been removed and a different residue inserted in its place. Such substitutions are generally conservative substitutions when it is desired to finely modulate the characteristics of the protein. Examples of such conservative substitutions are well known, and are shown, for example, in U.S. Pat. No. 5,928,896 and U.S. Pat. No. 5,917,019.

Substantial changes in function or immunological identity are made by selecting substitutions that are less conservative i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

EXAMPLE 6

Figure 10:
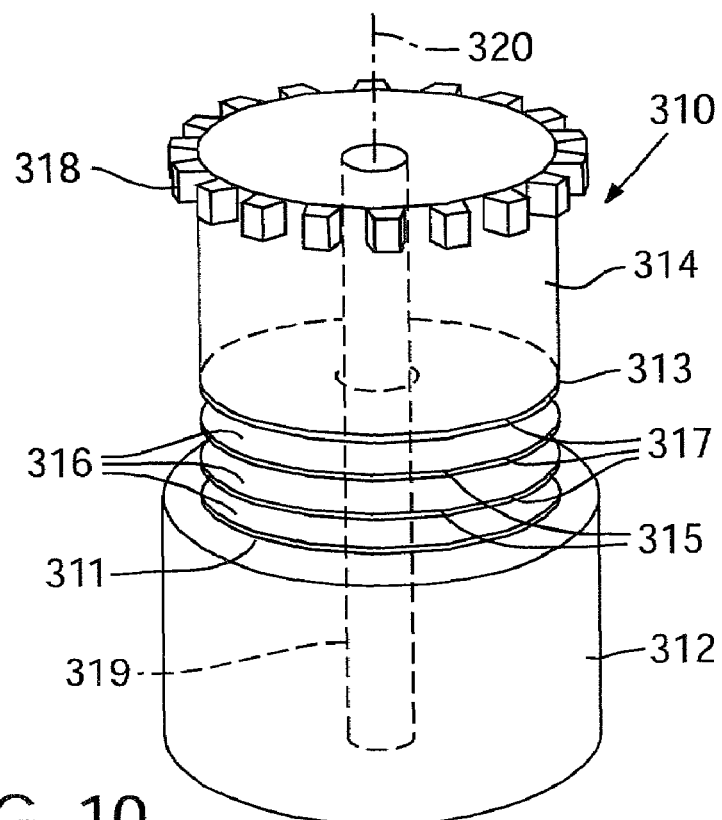
FIG. 10 is a schematic illustration of another embodiment of the molecular motor wherein actin and myosin, respectively, are coated on opposing axially aligned annular substrate surfaces.

An embodiment of a molecular motor 310 that includes annular substrates is depicted in FIG. 10. Discs are shown as the annular substrates in FIG. 10, but a layer of concentric rings lying in a common plane may be substituted for each one of the discs. These rings and ring layers are shown in detail in FIG. 13.

With reference to FIG. 10, a planar surface of a first disc 311 is secured to a base 312 so that the first disc 311 is not free to rotate relative to the base 312. The first disc 311 may be secured to the base 312 by any suitable manner such as by an adhesive. A second disc 313 is secured to a drive member 314 so that the second disc 313 is free to rotate relative to the first disc 311. The second disc 313 may be secured to the drive member 314 by any suitable manner such as by an adhesive. The drive member 314 may include a series of gear teeth for driving a driven member similar to that shown in FIG. 1. The first disc 311 and the second disc 313 are axially aligned relative to each other along a central longitudinal axis 320. The first disc 311 and the second disc 313 each define a respective orifice (depicted, for example, as element 352 in FIG. 12A or as element 372 in FIG. 12B) centered on the central axis 320. The orifices receive a support rod 319 that is axially aligned along the central axis 320. The support rod 319 is secured by the base 312 so that the support rod 319 is not free to rotate relative to the base 312. The support rod 319 is received within the drive member 314 so that the drive member 314 and second disc 313 remain free to rotate relative to the support rod 319. Bushings or ball bearings (not shown) may be provided at the surface interfaces between the support rod 319 and the drive member 314, and between the support rod 319 and the second disc 313 to allow the relative rotation. The support rod 319 assists in maintaining the radial alignment of the discs.

Myosin is coated on a planar surface 316 of the first disc 311 that is obverse to the disc surface secured to the base 312. Actin is coated on a planar surface 317 of the second disc 313 that is obverse to the disc surface secured to drive member 314. In one embodiment (not shown) the myosin-coated surface 316 of the first disc 311 opposes, and is sufficiently close to, the actin-coated surface of the second disc 313 such that the myosin and actin interact to rotate the second disc 313 relative to the first disc 311.

In another embodiment, at least one freely rotating intermediate disc 315 is disposed between the first disc 311 and the second disc 313. The intermediate disc 315 includes a first planar surface that is coated with myosin 316 and an obverse second planar surface that is coated with actin 317. The first disc 311, intermediate disc(s) 315, and second disc 313 are arranged such that each myosin-coated surface 316 is positioned adjacent to, or opposes, an actin-coated surface 317. The myosin-coated surfaces 316 and the actin-coated surfaces 317 are sufficiently close to each other so that the myosin and actin interact to rotate the intermediate disc(s) 315 relative to each other and the first disc 311. The intermediate disc 315 located adjacent to the second disc 313 rotates the second disc 313. Although the first disc 311 is depicted in FIG. 10 as the only disc directly affixed to a drive member, the intermediate disc(s) 315 could also be directly coupled to a drive member or power take-off. For example a drive belt (not shown) could be coupled to the peripheral edge of the intermediate disc(s) 315 or the peripheral edge of the intermediate disc(s) 315 could define a series of gear teeth (not shown). Another feature of multiple stacked discs is that the discs could be configured to multiply the rotational speed of the second disc 313 in a manner analogous to the embodiment shown in FIG. 6. In other words, the difference between the rotational velocity of the second disc 313 and the rotational velocity of the intermediate disc 315 located the farthest distance from the second disc 313 is directly proportional to the number of stacked discs.

During operation, a liquid containing a sufficient concentration of ATP is introduced between the respective planar surfaces of the discs. The myosin coated on the disc surface (s) 316 undergoes a conformation change to attach to, and move, an adjacent actin-coated disc surface(s) 317. Movement of the actin-coated disc surface(s) 317 moves any drive member(s) coupled to such discs.

An optional outer cylinder (not shown) encompassing the discs may assist in directing the ATP-containing liquid to the appropriate location. The outer cylinder may optionally include perforations for introducing the ATP-containing liquid into the cylinder's interior. Alternatively, the ATP-containing liquid could be introduced via openings (not shown) provided in the central support rod 319. The discs may be constructed to facilitate the flow of the ATP-containing liquid.

Figure 12A:
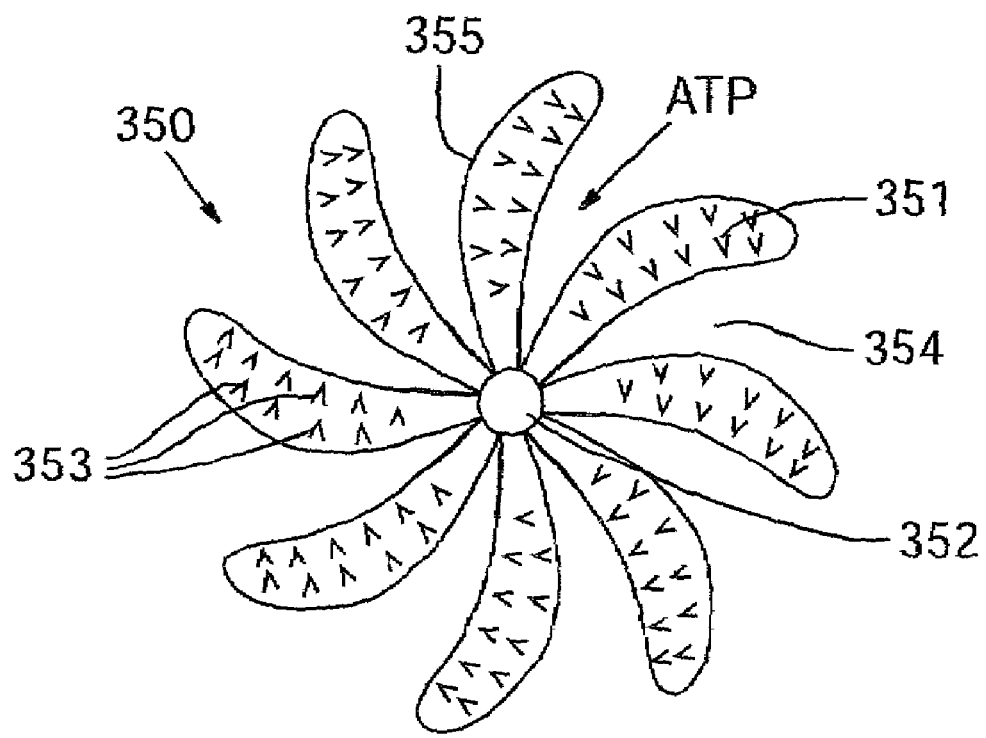
FIGS. 12A and 12B are each plan views of disc embodiments that could be used in the molecular motor shown in FIG. 10 or 11.

For example, FIG. 12A shows a representative disc embodiment 350 that includes voids or perforations 354 arranged circumferentially around the disc orifice 352. The voids 354 may be designed such that they have a wide opening at the peripheral edge of the disc 350 tapering down to a closed end at the edge of the disc orifice 352. Such a design results in propeller-shaped disc blades 351 arranged circumferentially around the disc orifice 352. Each propeller-shaped disc blade may have a leading edge 355 that is swept back or arcuate in a direction corresponding to the rotation direction of the disc 350. Actin may be directionally applied to a surface of the disc blades 351 as represented by arrows 353. Of course, myosin may be coated on the surface rather than actin. As the disc 350 rotates clockwise, the ATP-containing liquid ("ATP" in FIGS. 12A and 12B) is swept in along the leading edges 355 of the disc blades 351 so that it contacts the actin-coated surfaces. The ATP-containing liquid would be drawn towards the center of the disc 350. The support rod 319 could be provided with openings (not shown) for receiving the waste ATP liquid and discharging it from the motor. Adjacent discs 350 with the propeller configuration should be designed so that there is overlap at all operating times between at least a portion of the adjacent disc blade 351 surfaces and, thus, contact between the motor proteins. For example, the voids 354 could be smaller than the disc blades 351 or the voids 354 could have a different geometric shape relative to the geometric shape of the disc blades 351.

Figure 12B:
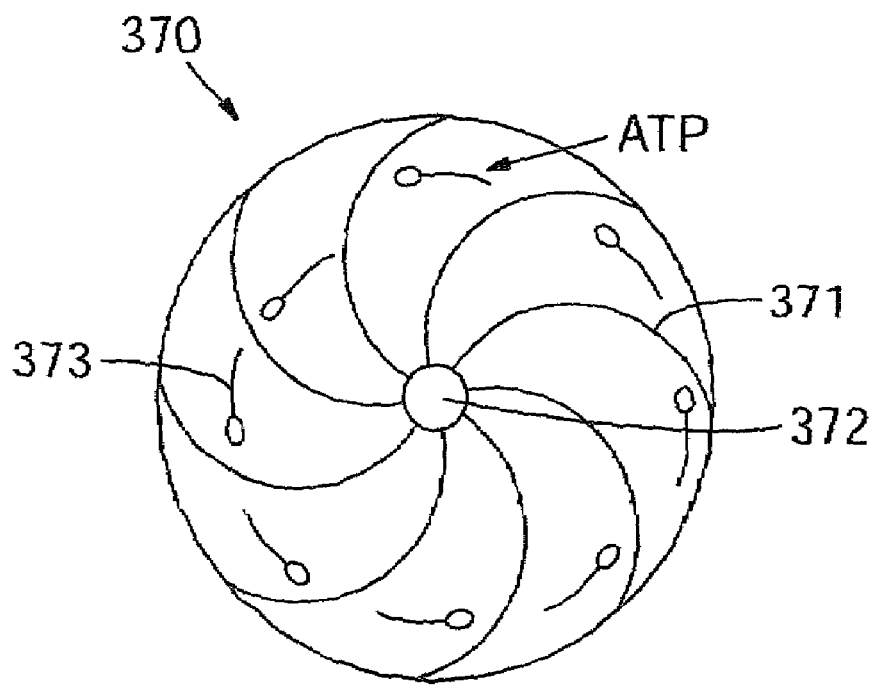

FIG. 12B shows another representative disc embodiment 370 that includes grooves or indentations 371 formed on a surface of the disc 370 that is coated with myosin molecules 373. The grooves 371 could extend from the peripheral edge of the disc 370 to the edge of the disc orifice 372. The grooves 371 are swept back or arcuate to facilitate flow of the ATP-containing liquid across the surface of the disc 370 and towards the center of the disc 370 as the disc 370 rotates clockwise. The support rod 319 could be provided with openings (not shown) for receiving the waste ATP liquid and discharging it from the motor. The grooves 371 are shown in FIG. 12B as continuous grooves but could be discontinuous grooves.

Figure 13:
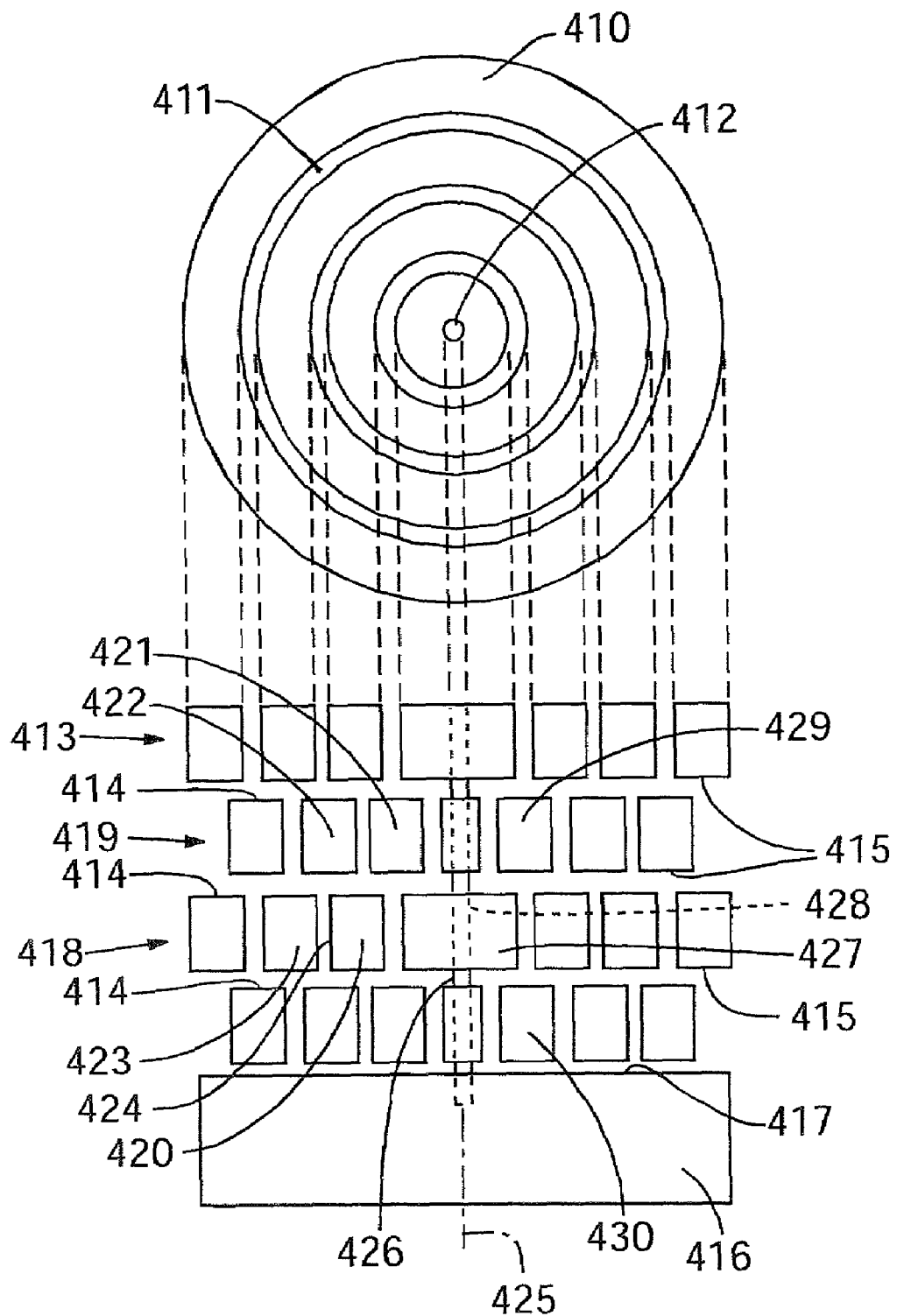
FIG. 13 is a schematic view of a molecular motor embodiment similar to that shown in FIG. 10 or 11 wherein rings are substituted for the discs.

As mentioned above, the discs depicted in FIG. 10 could be replaced by rings as illustrated in FIG. 13. At least two concentric rings 410 lie in a common plane around a central orifice 412 to form a ring layer 413. The rings 410 may be rigid or flexible. A stationary central support rod 426 is received within the central orifice 412. Each ring layer 413 includes a central ring 427 that defines an annular inner surface 428 that is fixedly secured to the surface of the central support rod 426. The central support rod 426 and the central rings 427 may form an integral member. One end of the central support rod 426 is fixedly secured to a base 416. The common plane of each ring layer 413 is transverse to a longitudinal axis 425. The ring layers 413 are located axially adjacent each other along the longitudinal axis 425. With reference to FIG. 13, "axially" or "axial" denotes a direction parallel to the longitudinal axis 425 and "radially" or "radial" denotes a direction transverse to the longitudinal axis 425. A first planar surface 414 of the ring 410 is coated with a motor protein such as, for example, myosin. An obverse second planar surface 415 of the ring 410 is coated with a complementary motor protein such as, for example, actin. A gap 411 is provided between adjacent rings 410. The support rod 426 and concentric ring arrangement assist in maintaining the radial alignment of the rings 410. Each ring 410 (except central rings 427) is free to rotate relative to any other ring 410 and relative to the stationary support rod 426.

At least two, more particularly at least three, ring layers 413 are disposed adjacent to each other, for example, in a stacked configuration, such that the myosin-coated surfaces 414 oppose the actin-coated surfaces 415. A base 416 defining a surface 417 is provided adjacent to a bottom ring layer. Ball bearings or similar friction reducing materials may be provided on the surface 417. Drive member(s) (not shown) may be coupled to any of the rotating rings 410 in a manner similar to those described above in connection with the other embodiments.

The location of each gap 411 in a given ring layer is radially offset from the location of each gap 411 in adjacent ring layers. Consequently, each individual ring 410 can assist in directly driving or powering two rings 410 in the adjacent ring layers 413. Such cooperation between the rings is illustrated by examining a given ring 420 in a given ring layer 418. Rotation of ring 420 will drive both rings 422 and 421 in adjacent ring layer 419 since the myosin-coated surface 414 of ring 420 contacts a portion of the actin-coated surface 415 of ring 422 and a portion of the actin-coated surface 415 of ring 421. Ring 422 in ring layer 419 in turn drives ring 423 in ring layer 418. Each central ring (e.g., ring 427) is stationary. Thus, the myosin-coated surface 414 of central ring 427 drives the actin-coated surface 415 of the innermost freely rotating ring 429 in adjacent ring layer 419. Similarly, the actin-coated surface 415 of central ring 427 drives the myosin-coated surface 414 of ring 430 in the other adjacent layer. In this arrangement, the outer rings will have greater rotational speeds than the inner rings.

Opposing curved surfaces (e.g., surface 424) between adjacent rings (e.g., rings 420 and 423) in the same layer may also be coated with complementary motor proteins so that all rings surfaces can contribute to the drive power.

Similar to the above-described embodiment, a liquid containing a sufficient concentration of ATP is introduced between the respective planar surfaces of the ring layers. The myosin coated on the surface(s) 414 undergoes a conformation change to attach to, and move, an adjacent actin-coated surface 415. The drive cooperation among the individual rings permits 410 substantial radial narrowing of the planar surfaces 414, 415 of the rings 410. The decreased radial width means that substantially uniform rotational velocities are present across the planar surfaces 414, 415 of each ring 410. Consequently, the motor protein interaction across the planar surfaces 414, 415 can occur at optimum uniform speeds, thus improving the efficiency of the motor.

An optional outer cylinder (not shown) encompassing the ring layers 413 may assist in directing the ATP-containing liquid to the appropriate location. The outer cylinder may optionally include perforations for introducing the ATP-containing liquid into the cylinder's interior. Alternatively, the ATP-containing liquid could be introduced via openings (not shown) provided in the central support rod 426. The planar surfaces 414, 415 of the rings 410 may be provided with grooves as described in connection with FIG. 12B to facilitate the flow of the ATP-containing liquid. The outermost peripheral rings 410 could be affixed to the outer cylinder and, thus, the outer cylinder could be coupled to a drive member (not shown) in a manner similar to that shown in FIG. 1.

Figure 11:
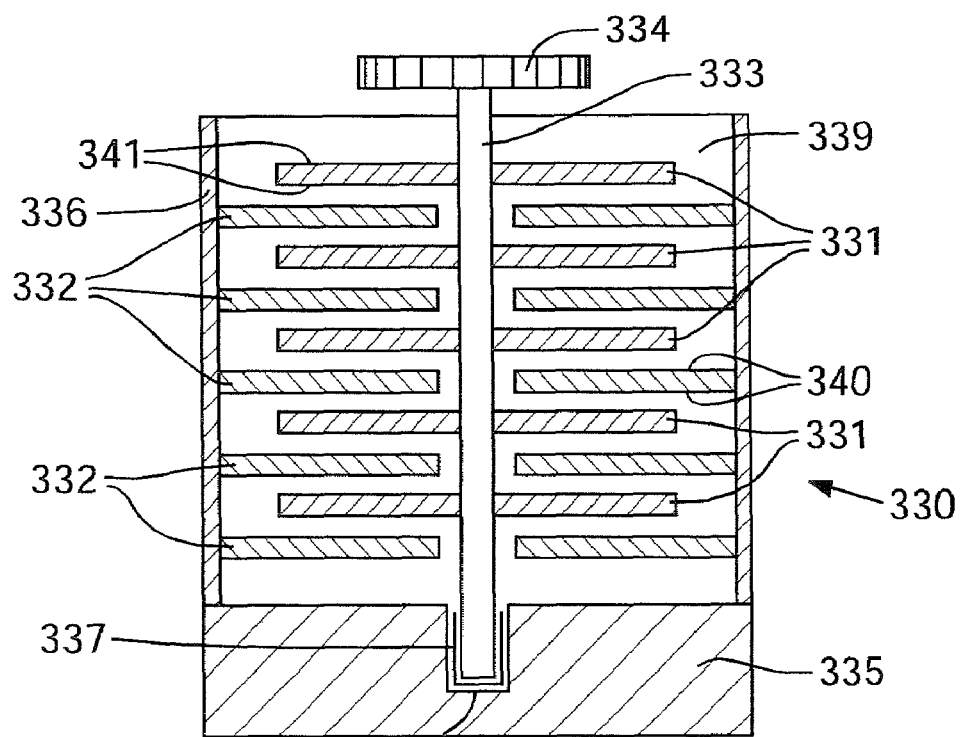
FIG. 11 is a cross-section side view of a further embodiment of a molecular motor that includes discs coated with actin and myosin.

FIG. 11 illustrates another molecular motor 330 embodiment that includes interdigitated discs. A stationary hollow cylinder 336 is supported on a base 335 and defines an internal void 339 that receives a drive shaft 333. A mounting element 337 is received within a cavity 338 defined in the base 335. The mounting element 337 rotatably secures the drive shaft 333 to the base 335. A drive member 334 is coupled to the drive shaft 333 in any suitable manner. The drive member 334 may define gear teeth, support a drive belt, or be configured in any similar manner to provide useful work.

At least one outer disc 332 is mounted onto the inner surface of the stationary cylinder 336. Planar surfaces 340 of the outer disc(s) 332 may be coated with myosin or, alternatively, actin. The outer disc(s) 332 defines a central orifice receiving the drive shaft 333. The central orifice is designed to allow the drive shaft 333 to rotate freely relative to the stationary outer disc(s) 332. For example, the circumference of the central orifice may be sufficiently greater than the circumference of the drive shaft 333 so that no contact can occur or, alternatively, bushings, ball bearings or similar devices may be located at the orifice edge/drive shaft edge interface.

At least one inner disc 331 is also disposed in the void 339. Planar surfaces 341 of the inner disc(s) 331 may be coated with actin or, alternatively, myosin. If the surfaces 341 of the inner disc(s) are coated with actin, then the surfaces 340 of the outer disc(s) 332 should be coated with myosin. The inner disc(s) 331 and outer discs(s) 332 are arranged in an alternating pattern, and sufficiently close to each other, so that the actin and myosin can interact together in the presence of ATP. The inner disc 331 defines a central orifice as shown, for example, in FIGS. 12A and 12B. The drive shaft 333 is received in the central orifice and is affixed to the inner disc 331 at the edges of the central orifice.

During operation, a liquid containing a sufficient concentration of ATP is introduced between the respective planar surfaces of the discs. The actin and myosin interact with each other as described above. Movement of the actin layer attached to the inner disc(s) 331 results in rotation of the drive shaft 333 and drive member 334 relative to the stationary cylinder 336 and stationary outer disc(s) 332.

A variant (not shown) of the motor 330 illustrated in FIG. 11 could include an outer cylinder and attached outer disc(s) that could rotate relative to a stationary inner support rod and attached inner disc(s). The rotatable outer cylinder would be coupled to the drive member.

Figure 14:
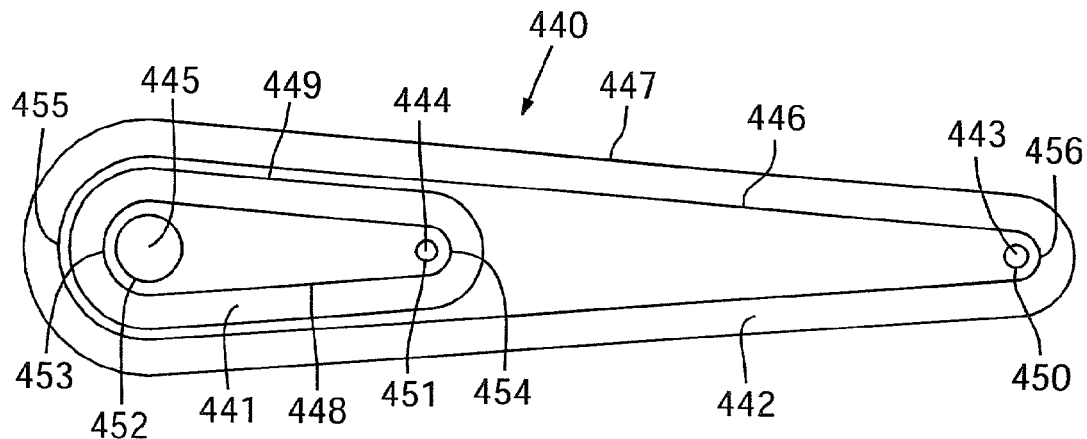
FIG. 14 is a cross-section side view of another variant of the molecular motor depicted in FIG. 1 or FIG. 2.
Figure 15:
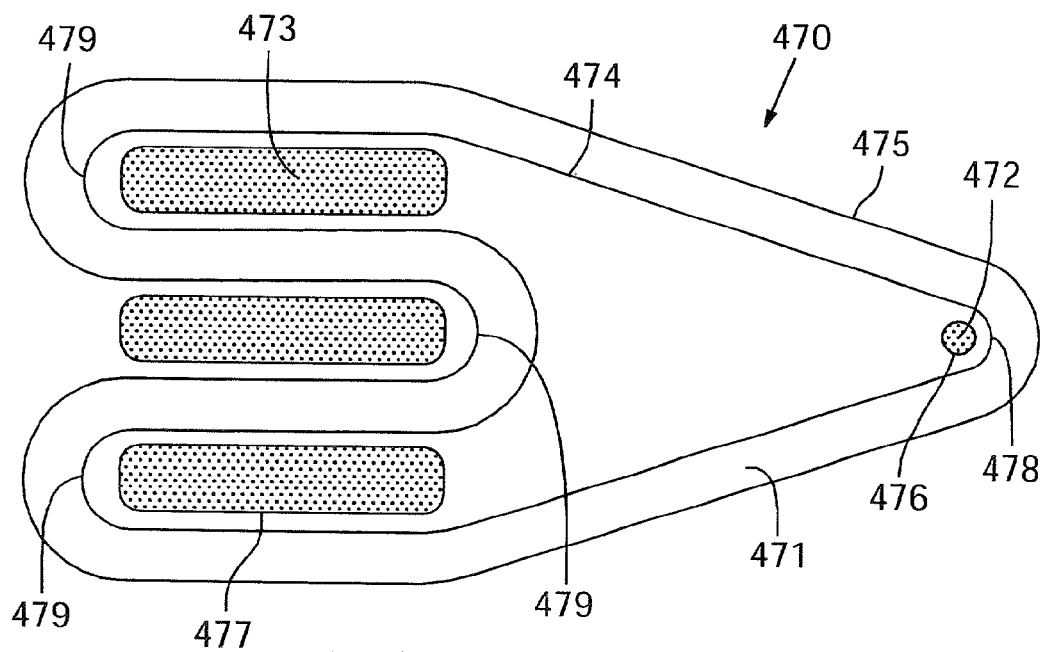
FIG. 15 is a cross-section side view of a further variant of the molecular motor depicted in FIG. 1 or FIG. 2.

Variants of the above-described cylinder or cone embodiments are shown in FIGS. 14 and 15. In each of these variants, at least one continuous loop of a flexible substrate follows an elongated cylindrical, oblong, elliptical, serpentine or similar multiple turning radii rotation path. The flexible substrate can be, for example, a tape or thread, made from a compliant material such as a fibrous material. The continuous loop is supported by, and/or the rotation path is directed by, at least two rotation loci members such as another nested continuous loop (that, in turn, includes at least two rotation loci), cylinders or stanchions. One of the rotation loci members defines a surface that drives the continuous loop as detailed below. The rotation loci members are located at internal and/or external turning radii defined by the continuous loop.

With reference to FIG. 14, a molecular motor 440 is shown that includes a first cylinder 445 and a second cylinder 444 disposed, respectively, within a first internal radius 453 and a second internal radius 454 defined by a first flexible loop substrate 441. The first flexible loop substrate 441 defines an inner surface 448 and an outer surface 449. The inner surface 448 is in contact with, and supported by, peripheral surface 452 of first cylinder 445 and peripheral surface 451 of second cylinder 444. The first loop substrate 441 is disposed within a first internal radius 455 of a second flexible loop substrate 442. A third cylinder 443 is disposed within a second internal radius 456 of the second loop substrate 442. The second loop substrate 442 defines an inner surface 446 and an outer surface 447. The inner surface 446 is in contact with, and supported by, peripheral surface 450 of third cylinder 443 and the outer surface 449 of the first loop substrate 441. At least one of the second and third cylinders 444, 443 are rotatable and may be coupled to a drive member (not shown) in a manner similar to that depicted, for example, in FIG. 1. First cylinder 445 is stationary. At least one of the first, second and third cylinders 445, 444, 443 also may be extended and coupled to a base member (not shown) for supporting the molecular motor 440. A drive member such as a belt (not shown) may also be engaged with the outer surface 447 of the second loop substrate 442.

The peripheral surface 452 of the first cylinder 445 is coated with a motor protein (e.g., myosin) and the inner surface 448 of the first loop substrate 441 is coated with a complementary motor protein (e.g., directionally applied actin). The outer surface 449 of the first loop substrate 441 also is coated with a motor protein (e.g., directionally applied actin) and the inner surface 446 of the second loop substrate 442 is coated with a complementary motor protein (e.g., myosin). The actin/myosin interaction upon exposure to ATP moves the first loop substrate 441 relative to the second loop substrate 442. Movement of the first loop substrate 441 and/or second loop substrate 442 rotates at least one of the second or third cylinders 444, 443. Second loop substrate 442 may be provided with perforations (not shown) for introducing an ATP-containing liquid between the inner surface 446 of the second loop substrate 442 and the outer surface 449 of the first loop substrate 441.

Additional nested loop substrates may be provided to increase the rotational velocity of the outer loop substrate. Increasing the width of the loop substrates can increase the power of the molecular motor 440.

With reference to FIG. 15, a molecular motor 470 is shown that includes a cylinder 472 disposed within a first internal radius 478 defined by a flexible loop substrate 471. A plurality of stationary posts or stanchions 473 are disposed within second radii 479 defined by the loop substrate 471. According to particular embodiments, there are at least three posts 473 so that the loop substrate follows a serpentine path. Each post 473 defines an outer surface 477. The loop substrate 471 defines an inner surface 474 and an outer surface 475. The inner surface 474 is in contact with, and supported by, peripheral surface 476 of cylinder 472 and the outer surfaces 477 of the posts 473. The cylinder 472 may be stationary or rotatable. If the cylinder 472 is rotatable, it may be coupled to a drive member (not shown). A drive member (not shown) may also be engaged with the loop substrate 471. For example, the edges of the loop substrate 471 may define gear teeth (not shown) for engaging with a driven member (not shown). Such gear teeth may also assist in supporting the molecular motor 470.

The outer surface 477 of each stationary post 473 is coated with a motor protein (e.g., myosin). The inner surface 474 and the outer surface 475 of the loop substrate 471 are coated with a complementary motor protein (e.g., directionally applied actin). The actin/myosin interaction upon exposure to ATP moves the loop substrate 471 relative to the posts 473 and, thus, moves any coupled drive members. The loop substrate 471 may be provided with perforations (not shown) for introducing an ATP-containing liquid between the surfaces 474, 475 of the loop substrate 471 and the outer surfaces 477 of the posts 473. Increasing the width of the loop substrate 471, the contact length between the outer surfaces 477 of the posts 473 and the surfaces 474, 475 of the loop substrate 471, and/or increasing the number of posts 473 can increase the power of the molecular motor 470.

The motor protein-coated loop substrate shown in the embodiments of FIGS. 14 and 15 can be made by passing the loop substrate through a bath(s) that includes the desired motor protein. The motor protein-coated loop substrate may be placed around the support cylinders. The tension of each individual loop then may be adjusted accordingly.

In view of the many possible embodiments to which the principles of our disclosure may be applied, it should be recognized that the illustrated embodiment is only a particular example of the disclosure and should not be taken as a limitation on the scope of the disclosure. Rather, the scope of the disclosure is defined by the following claims.

We claim:

1. A molecular rotary motor comprising:
   a first array of a first motor molecule wherein the first motor molecule is disposed upon a first surface; and
   a second array of a second motor molecule wherein the second motor molecule is disposed upon a second surface of a cylinder, shaft or cone wherein the cylinder, shaft or cone has a longitudinal rotation axis, the second surface being different from the first surface, and
   wherein the first and second arrays are in sufficiently close contact to interact and rotate the second surface around the longitudinal rotation axis of the cylinder, shaft or cone, and the first motor molecule and the second motor molecule are each directionally aligned with respect to each other such that orientation of the second motor molecule directs movement of the second surface, the second motor molecule being directionally aligned substantially perpendicular to the longitudinal rotation axis of the cylinder, shaft or cone.

2. The molecular motor of claim 1, further comprising a driven member rotatable by the interaction between the first array and the second array.

3. The molecular motor of claim 1, wherein the first array and the second array comprise multiple nested arrays that interact with one another to rotate relative to one another.

4. The molecular motor of claim 1, wherein the first surface comprises a first curved surface and the second surface comprises a second curved surface.

5. The molecular motor of claim 4, wherein the first and second curved surfaces are continuous curved surfaces.

6. The molecular motor of claim 5, wherein the first and second curved surfaces are complementary shaped cylindrical or conical surfaces.

7. The molecular motor of claim 6, further comprising a first nested member and a second nested member, wherein the first and second curved surfaces are complementary curved surfaces of the first and second nested members.

8. The molecular motor of claim 1, wherein the first motor molecule is myosin and the second motor molecule is actin.

9. The molecular motor of claim 1, further comprising a source of ATP.

10. The molecular motor of claim 1, wherein the first and second surfaces comprise perforations to allow permeation of a liquid fuel source to the motor molecules.

11. The molecular motor of claim 1, wherein the first array is coated on a first curved surface, and the second array is coated on a second curved surface.

12. The molecular motor of claim 1, wherein one of the arrays is coated on an outer surface of a cylinder, shaft or cone, and another of the arrays is coated on an inner surface of a surrounding structure having a complementary shape that substantially conforms to a shape of the outer surface of the cylinder, shaft or cone.

13. The molecular motor of claim 1, wherein the interaction between the first array and the second array rotates a driver.

14. The molecular motor of claim 13, wherein the driver is an internal shaft or cylinder in the motor.

15. The molecular motor of claim 13, wherein the driver is an outer curved surface of the motor.

16. A motor comprising:
a first array of a first motor molecule;
a second array of a second motor molecule disposed upon a surface of a cylinder, shaft or cone wherein the cylinder, shaft or cone has a longitudinal rotation axis; and
a driven member moved by the directional movement of the second surface,
wherein the first and second arrays of motor molecules are in sufficiently close contact to interact and rotate the surface around the longitudinal rotation axis of the cylinder, shaft or cone, and
wherein the driven member is a rotating shaft, a propeller, a wheel, a lever-arm, a gear system, or a pulley system.

17. The molecular motor of claim 1, wherein predetermined dimensions of the first and second arrays determine a power output of the motor.

18. The molecular motor of claim 17, wherein the predetermined dimensions are lengths of the first and second arrays.

19. The molecular motor of claim 3, wherein a predetermined number of nested arrays are provided to select a speed of rotation of the motor.

20. The molecular motor of claim 1, further comprising a supply of a fuel source, wherein the supply of the fuel source is used to activate rotation of the second surface relative to the first surface.

21. The molecular motor of claim 20, wherein the supply of the fuel source is a regulated supply of the fuel source.

22. The molecular motor of claim 21, wherein the regulated supply of the fuel source is regulated by a switch or a valve.

23. The molecular motor of claim 20, wherein the fuel source is ATP.

24. A molecular motor comprising:
a first array of a first motor molecule disposed on a first surface;
a second array of a second motor molecule disposed on a second surface of a cylinder, shaft or cone wherein the cylinder, shaft or cone has a longitudinal rotation axis, wherein the second motor molecule interacts with the first motor molecule to move directionally relatively to the first motor molecule; and
at least one perforation in the first or second surface to allow permeation of a liquid fuel source through the surface to the motor molecules,
wherein the first and second arrays of motor molecules are in sufficiently close contact to interact and rotate the second surface around the longitudinal rotation axis of the cylinder, shaft or cone.

25. The molecular motor of claim 24, wherein the first motor molecule is myosin and the second motor molecule is actin and the actin is applied directionally to the second surface such that orientation of the actin directs movement of the second surface.

26. The molecular motor of claim 1, wherein the first array is coated on a planar surface of a first annular substrate and the second array is coated on a planar surface of a second annular substrate.

27. The molecular motor of claim 26, wherein the coated planar surface of the first annular substrate is adjacent to the coated planar surface of the second annular substrate.

28. The molecular motor of claim 26, further comprising a driver coupled to the second annular substrate and wherein rotational movement of the second surface rotates the driver.

29. The molecular motor of claim 1, wherein at least one of the first surface or the second surface comprises at least one planar surface of an annular substrate.

30. The molecular motor of claim 24, wherein the first or second surface comprises at least one planar surface of an annular substrate.

31. The molecular motor of claim 1, wherein at least one of the arrays is coated on a continuous loop of a flexible substrate.

32. The molecular motor of claim 31, wherein the continuous loop rotates along an elongated cylindrical, oblong, elliptical, or serpentine path.

33. A motor comprising:
a first array of a first motor molecule disposed on a curved surface of a first cylinder, first shaft or first cone, wherein the first cylinder, first shaft or first cone has a longitudinal rotation axis;
a second array of a second motor molecule disposed on a second surface,
wherein the first and second arrays are in sufficiently close contact to interact and rotate the second surface around the longitudinal rotation axis of the cylinder, shaft or cone, or to interact and rotate the curved surface of the cylinder, shaft or cone around the longitudinal rotation axis.

34. The motor of claim 33, wherein the first array of the first motor molecule is disposed on the surface of a cylinder.

35. The motor of claim 34, wherein the second surface is a curved surface complementary to the surface of the cylinder.

36. The motor of claim 33, further comprising a driven member moved by the directional movement of the second surface or the surface of the cylinder, shaft or cone.

37. The motor of claim 33, wherein the first and second motor molecules are proteins.

38. The motor of claim 33, wherein the first motor molecule is myosin and the second motor molecule is actin.

39. The motor of claim 33, wherein the first motor molecule is kinesin and the second motor molecule is a microtubule.

40. The motor of claim 33, wherein the second surface is a curved surface complementary to the curved surface of the cylinder, shaft or cone.

41. The molecular motor of claim 1, wherein the second surface is configured to rotate through at least one complete rotation relative to the first surface.

42. The molecular motor of claim 1, wherein the first and second motor molecules are proteins.

43. The molecular motor of claim 1, wherein the first motor molecule is kinesin and the second motor molecule is a microtubule.

44. The motor of claim 16, wherein the first motor molecule is kinesin and the second motor molecule is a microtubule.

45. The molecular motor of claim 24, wherein the second surface is a surface of a cylinder.

46. The molecular motor of claim 24, wherein the first and second motor molecules are proteins.

47. The molecular motor of claim 24, wherein the first motor molecule is kinesin and the second motor molecule is a microtubule and the second motor molecule is applied directionally to the second surface such that orientation of the microtubule directs movement of the second surface.

48. The molecular motor of claim 24, wherein the second array and the second surface are configured to rotate relative to the first array and the first surface.

49. The molecular motor of claim 1, wherein the second surface is rotatable relative to the first surface in a rotational direction that substantially parallels the directional alignment of the second motor molecule.

50. The motor of claim 33, wherein the second surface is rotatable relative to the surface of the cylinder, shaft or cone.

51. The motor of claim 33, wherein the surface of the cylinder, shaft or cone is rotatable relative to the second surface.

52. The molecular motor of claim 2, wherein the driven member is rotatable in a rotational direction that substantially parallels the directional alignment of the second motor molecule.

53. The molecular motor of claim 16, wherein the second motor molecule is directionally aligned substantially perpendicular to the longitudinal rotation axis.

54. The motor of claim 33, wherein the second surface is a surface of a second cylinder, second shaft or second cone.

55. The motor of claim 54, wherein the second cylinder, second shaft or second cone has a longitudinal axis that is the same as the longitudinal rotation axis of the first cylinder, first shaft or first cone, and the first motor molecule and the second motor molecule are directionally disposed on the first surface and the second surface, respectively, substantially perpendicular to the longitudinal rotation axis.

56. The motor of claim 1, wherein the second motor molecule is rotatable in a rotational direction that substantially parallels the directional alignment of the second motor molecule.

57. The motor of claim 33, wherein the first motor molecule and the second motor molecule are directionally aligned with each other such that orientation of the first motor molecule relative to orientation of the second motor molecule directs movement of the second motor molecule relative to the first motor molecule.

58. The motor of claim 57, wherein rotation of the second surface or the curved surface is in the same direction as the directional alignment of the first motor molecule and the second motor molecule.

59. The motor of claim 1, wherein the second surface rotates relative to the first surface.

60. The motor of claim 16, wherein the second array rotates relative to the first array.

* * * * *